United States Patent
Huang et al.

(10) Patent No.: US 11,202,835 B2
(45) Date of Patent: Dec. 21, 2021

(54) METHOD OF CONTROLLED COMPETITIVE EXCHANGE

(71) Applicant: Anteo Technologies Pty Ltd, Eight Mile Plains (AU)

(72) Inventors: Chang-Yi Huang, Calamvale (AU); Nobuyoshi Joe Maeji, Wishart (AU)

(73) Assignee: ANTEO TECHNOLOGIES PTY LTD, Eight Mile Plains (AU)

( * ) Notice: Subject to any disclaimer, the term of this patent is extended or adjusted under 35 U.S.C. 154(b) by 150 days.

(21) Appl. No.: 15/777,327

(22) PCT Filed: Nov. 21, 2016

(86) PCT No.: PCT/AU2016/051132
§ 371 (c)(1),
(2) Date: May 18, 2018

(87) PCT Pub. No.: WO2017/083938
PCT Pub. Date: May 26, 2017

(65) Prior Publication Data
US 2018/0333500 A1  Nov. 22, 2018

(30) Foreign Application Priority Data

Nov. 20, 2015 (AU) ................................ 2015904802
Nov. 20, 2015 (AU) ................................ 2015904803

(51) Int. Cl.
| | |
|---|---|
| *A61K 47/61* | (2017.01) |
| *A61K 47/54* | (2017.01) |
| *G01N 30/06* | (2006.01) |
| *B01D 15/38* | (2006.01) |
| *A61K 47/59* | (2017.01) |
| *A61K 31/496* | (2006.01) |
| *A61K 38/16* | (2006.01) |
| *A61K 39/395* | (2006.01) |
| *C07K 16/18* | (2006.01) |

(52) U.S. Cl.
CPC ............ *A61K 47/61* (2017.08); *A61K 31/496* (2013.01); *A61K 38/16* (2013.01); *A61K 39/3955* (2013.01); *A61K 47/54* (2017.08); *A61K 47/59* (2017.08); *B01D 15/3828* (2013.01); *C07K 16/18* (2013.01); *G01N 30/06* (2013.01)

(58) Field of Classification Search
CPC ........ A61K 47/61; A61K 47/54; A61K 47/59; A61K 31/496; A61K 38/16; A61K 39/3955; B01D 15/3828; C07K 16/18; G01N 30/06
See application file for complete search history.

(56) References Cited

U.S. PATENT DOCUMENTS

2007/0264664 A1* 11/2007 Akhavan-Tafti ...........................
G01N 33/54306
435/6.14

FOREIGN PATENT DOCUMENTS

| | | |
|---|---|---|
| WO | 2006/002472 | 1/2006 |
| WO | 2007/076580 | 7/2007 |
| WO | 2011/140590 | 11/2011 |
| WO | 2015/021509 | 2/2015 |

OTHER PUBLICATIONS

International Search Report and Written Opinion, PCT/AU2016/051132, dated Mar. 3, 2017, 12 pages.
Dolman Mem et al. Renal targeting of kinase inhibitors. International Journal of Pharmaceutics. May 2008: 364: 249-257.
Braich N and Codd R. Immobilized metal affinity chromatography for the capture of hydroxamate-containing siderophores and other Fe(III)-binding metabolites directly from bacterial culture supernatants. Analyst. Mar. 2008 133: 877-880.
Block H et al. Immobilized-metal affinity chromatography (IMAC): A review. Methods in Enzymology, 2009; 463: 439-473.
Ma Z and Moulton B. Recent advances of discrete coordination complexes and coordination polymers in drug delivery. Coordination Chemistry Reviews. Jan. 2011; 255: 1623-1641.
Renfrew AK. Transition metal complexes with bioactive ligands: mechanisms for selective ligand release and applications for drug delivery. Metallomics. May 2014; 6: 1324-1335.

\* cited by examiner

*Primary Examiner* — Tracy Vivlemore
*Assistant Examiner* — Nam P Nguyen
(74) *Attorney, Agent, or Firm* — Myers Bigel, P.A.

(57) ABSTRACT

The present invention relates to a method of controlled competitive exchange of a first agent bound to a metal coordination complex with a competing agent, with selection of the nature of the first agent allowing a tailoring of the binding strength and thereby allowing for a desired level of control for subsequent displacement by the selected competing agent. The method may be employed for release of therapeutic agents, sequestration of larger molecules from a sample, generation of a preferred binding surface and the like.

20 Claims, 8 Drawing Sheets

METHOD OF CONTROLLED COMPETITIVE EXCHANGE

FIELD OF THE INVENTION

The invention relates to the competition between different molecules for available metal coordination sites in metal complexes and particularly polymeric metal complexes. Controlled competition between smaller molecule ligands and larger macromolecules having a multiplicity of ligands is demonstrated with applications in controlled release and/or sequestration of one ligand in preference to another and in temporary protection of binding surfaces.

BACKGROUND TO THE INVENTION

Any reference to background art herein is not to be construed as an admission that such art constitutes common general knowledge in Australia or elsewhere.

There are many different approaches to achieving the controlled release of therapeutics in vivo including coating of the therapeutic with, for example, an enteric coating which slowly breaks down thereby releasing the molecule systemically. Embedding the therapeutic within a polymeric matrix is also employed which allows it to be released at a rate which is dependent on its physical properties, thereby controlling its diffusion out of the matrix. Encapsulation of therapeutics within vesicles is also common and, depending on the nature of the vesicle, drug release may come about through degradation of the vesicle structure or diffusion of the drug out through appropriately sized pores in the vesicle wall.

While such approaches are in common use they each have drawbacks in terms of one or more of their ease of preparation, level of control and degree of applicability to a wide range of therapeutic molecules of differing molecular weights.

There are also many different approaches to sample enrichment including, for example, size exclusion chromatography which uses molecular size to differentiate between the molecules. In this approach, the larger molecules are eluted first with the smaller molecules taking far longer to elute off the column. More selective enrichment of various molecules can also be achieved by affinity chromatography/extraction using antibodies being immobilised on suitable substrates. Depletion of highly abundant proteins from mixtures is a useful technique in proteomics research. In more large scale applications, larger molecules may be "contaminants" such as virus, bacteria or other cells that needs to be removed, for example, in water treatment.

There is always a need for alternative simple, general methods for preferential sequestration of larger molecules from a mixture of small and large molecules.

There are also applications where there is a need to temporarily protect or mask the properties of some material, such as in the transport of polar materials through a hydrophobic barrier, to improve miscibility or binding between different materials, or to change/control the reactivity of materials towards certain preferred directions. Temporary protecting groups that can be removed under controllable conditions to expose pre-existing characteristics of the underlying material would have many uses. The preparation of porous substrates for binding target molecule as opposed to cross-linking such substrates is one such application.

Further, none of the current approaches allow for fine control in both the release of a bound therapeutic, or other small molecules, and, if appropriate, the sequestration of agents in solution employing the same basic substrate. Such a level of flexibility would be useful and would result in a competitive exchange of agents which is not seen or suggested in the prior art.

SUMMARY OF INVENTION

It has been found that if metal coordination complexes, preferably polymeric metal coordination complexes, having pre-existing coordination with smaller ligands are exposed to molecules having a greater number of electron donating sites, greater coordination strength with the metal complex, greater avidity or multi-component binding will lead to an exchange reaction, assuming other parameters are kept constant.

Therefore, the present invention is predicated, at least in part, on the realisation that, for metal coordination complexes, binding of a multi-dentate ligand will be stronger than that of a mono-dentate ligand. This means that if a metal ion is coordinated with one or more mono-dentate ligands and is then exposed to multi-dentate ligands it is expected that the multi-dentate ligands will compete the mono-dentate ligands off from the metal over time, assuming other variables are kept constant. Similarly, an oligomeric metal coordination complex with coordinated small molecule ligands will, when exposed to a competing macromolecule having a greater number of coordination sites, lead to the bound small molecule ligands being exchanged for the competing macromolecule which is then coordinately bound itself.

The ability to control this competitive exchange process by selection of the initially bound agent and control of conditions under which it is bound, has a number of applications including, for example, in the controlled release of therapeutic molecules when they are coordinated to the metal coordination complex which is itself coated onto a suitable substrate. Exposure in the body to native proteins (e.g. one of a variety of macromolecular ligands) will result in such drug molecules being exchanged or competed off the substrate-bound oligomeric metal coordination complex and therefore being released to express their therapeutic effect. If a targeted approach is required then this competitive exchange of the therapeutic can be realised from an implantable substrate which can be located surgically within the patient's body in the target area or, if systemic release is desirable, an injectable substrate to thereby make the therapeutic systemically available.

Alternatively, when both small molecule and macromolecular ligands are exposed simultaneously to initially bound agent on metal complex activated substrates, and there is competition for the limited coordination sites on the substrate, co-operability of avidity binding for the macromolecules will out compete the small molecule ligands and so the macromolecules become preferentially bound or sequestered, leaving the small molecules remaining in solution and therefore preferentially enriched within the solution.

As an example, proteins can be selectively sequestered in this manner thereby allowing the selective enrichment of a small molecule, such as a steroid for example, in the sample which can then be better analysed without interference from the previously high excess of protein. In another example, competition for available coordination sites on a metal coordination complex-activated substrate between small molecule and macromolecular ligands can be used to preferentially sequester high-abundance proteins in proteomics research. By selection of initially bound first agent and control of conditions under which it is bound, it will be possible to determine a macromolecular threshold where there is effective competition under the desired exposure time and conditions.

Alternatively, an initially bound first agent that temporarily caps or masks a metal coordination complex may change the binding kinetics to a substrate and/or metal coordination complex which is itself coated onto a substrate, and can temporarily change the surface properties of the metal complex activated substrate, such as the wettability. This will also change the binding kinetics for any competing macromolecular agent as well as, potentially, the preferred orientation of this competing agent with respect to the substrate.

One further example of the application of such an initially bound first agent on a metal complex activated substrate is in the immobilisation of proteins on porous materials such as nitrocellulose. Proteins will passively bind to these kinds of materials to give a capture antibody for various applications including their use as lateral flow strips in diagnostic applications. However, such passive, uncontrolled binding leads to non-uniformity across the material and increased cross-linking by the protein within the pores can affect solvent flow and result in non-uniform protein functionality. However, as described herein, metal complexes forming coordination complexes with initially bound first agent, such as mono-dentate or other small molecule ligands, can be used to coat the internal surfaces of such porous substrates and this initially bound first agent will act to reduce or prevent cross-linking within the porous membrane by the metal complexes. This means that when a competing agent, such as a protein, is exposed to the internal surface it will compete off the first agent and allow binding to the metal complex in a slower, controlled manner compared with protein binding without first agent on the metal complex. In this manner, the internal surfaces of the substrate are functionalised for optimal subsequent binding without uncontrolled loss of binding capacity.

In one broad form, the invention resides in a method of controlled competitive exchange of a bound first agent and a competing agent including the steps of:

(a) providing a metal coordination complex, having the first agent bound thereto, optionally on a surface of a substrate; and (b) exposing the metal coordination complex with bound first agent to the competing agent in solution, to thereby allow the competing agent to exchange with the first agent and become preferentially bound to the metal coordination complex.

Suitably, the metal coordination complex is a polymeric metal coordination complex.

The first agent is not the pre-existing ligand, for example, the counter-ion base ligands, water molecules or other ligands existing on the metal coordination complex as a consequence of having been formed from the metal salt. Rather, this ligand will have been replaced by the first agent which is used to control binding of competing agent.

Therefore, in one embodiment, the first agent is not one which is used in the formation of the metal coordination complex or polymeric metal coordination complex.

According to an aspect of the invention, there is provided a method of controlled competitive exchange, on a substrate, of a bound first agent and a competing agent including the steps of:

(a) providing a metal coordination complex, having one or more ligands bound to the metal of the metal coordination complex;

(b) exposing the metal coordination complex with bound one or more ligands to the first agent, in solution, to thereby have the first agent exchange with the one or more ligands; and (c) exposing the metal coordination complex with bound first agent, coated on the substrate, to the competing agent in solution, wherein either the metal coordination complex of step (a) or the metal coordination complex with bound first agent of step (b) is coated onto the substrate, to thereby allow the competing agent to exchange with the first agent and become preferentially bound to the metal coordination complex on the substrate.

The one or more ligands of step (a) may be considered to be 'native', pre-existing' or 'coordinate' ligands in that these are the ligands present and bound to the metal at the point of formation of the metal coordination complex.

Preferably, the one or more ligands of step (a) are the ligands present and bound to the metal at the point of or immediately following formation of the oligomeric metal coordination complex.

In one embodiment, the method may be considered to be a method of controlled release of the first agent.

In this embodiment, the first agent may be a therapeutic agent.

In a further embodiment, the method may be considered to be a method of sequestration of the competing agent.

In this embodiment, the competing agent may be present in a sample along with at least one further binding agent.

Therefore, in one aspect of the broad form, there is provided a method of selective sequestration of a competing agent, onto a substrate, from a sample in the presence of a further binding agent including the steps of:

(a) providing a metal coordination complex having one or more ligands bound to the metal of the metal coordination complex;

(b) exposing the metal coordination complex with bound one or more ligands to a first agent, in solution, to thereby have the first agent exchange with the one or more ligands; and (c) exposing the metal coordination complex with bound first agent, coated on the substrate, to the sample comprising the competing agent and the further binding agent, wherein either the metal coordination complex of step (a) or the metal coordination complex with bound first agent of step (b) is coated onto the substrate and wherein the competing agent has a greater number of electron donating sites than each of the first agent and the further binding agent, to thereby allow the competing agent to preferentially exchange with the first agent and become preferentially bound to the metal coordination complex.

In another embodiment of the broad form, the method of controlled competitive exchange may be considered to be a method of altering or manipulating the binding kinetics of a metal coordination complex having bound first agent to a competing agent by which reactivity to a further competing agent, such as a target molecule, wettability or other surface properties of the metal coordination complex, optionally coated onto a substrate, are altered.

In this embodiment, the first agent may be a small molecule able to bind metal complexes.

In an alternative aspect of the broad form, the method may be a method of generating a binding layer on an internal surface of a substrate, this method including the steps of:
(a) providing a metal coordination complex having one or more ligands bound to the metal of the metal coordination complex;
(b) exposing the metal coordination complex with bound one or more ligands to a first agent, in solution, to thereby have the first agent exchange with the one or more ligands and become coordinately bonded to the metal; and
(c) coating the metal coordination complex having bound first agent onto the internal surface of the substrate,
to thereby generate the binding layer on the internal surface of the substrate.

In this embodiment, the exchange reaction may be considered to be between the substrate which is acting as a large competing agent and the first agent.

Further to the above, according to one particular aspect of the broad form, there is provided a method of capturing a competing agent on an internal surface of a substrate including the steps of:
(a) providing a substrate comprising an internal surface, the internal surface at least partially coated with a metal coordination complex having a bound first agent; and
(b) exposing the coated substrate with bound first agent to the competing agent in solution,
to thereby allow the competing agent to preferentially exchange with the first agent and become preferentially bound to the metal coordination complex, to thereby capture the competing agent on the internal surface of the substrate.

The coated substrate with bound first agent may be formed as described above for the method of generating a binding layer on an internal surface of a substrate and so the method may include each of those steps, as required.

The competing agent to be captured may be a target molecule.

In one embodiment, wherein the competing agent to be captured is a target molecule, the method may further include the step (a)(i) of exposing the coated substrate of step (a) to a capture molecule, as the competing agent, to displace the first agent and coordinately bond to the metal coordination complex, the capture molecule being capable of binding the target molecule.

According to a further aspect of the invention, there is provided a substrate having an internal surface comprising a binding layer, the binding layer comprising a metal coordination complex having a first agent coordinately bonded thereto.

The substrate with the internal surface comprising the binding layer may be formed as described above for the method of generating a binding layer on an internal surface of a substrate.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Definitions

Figure 1:
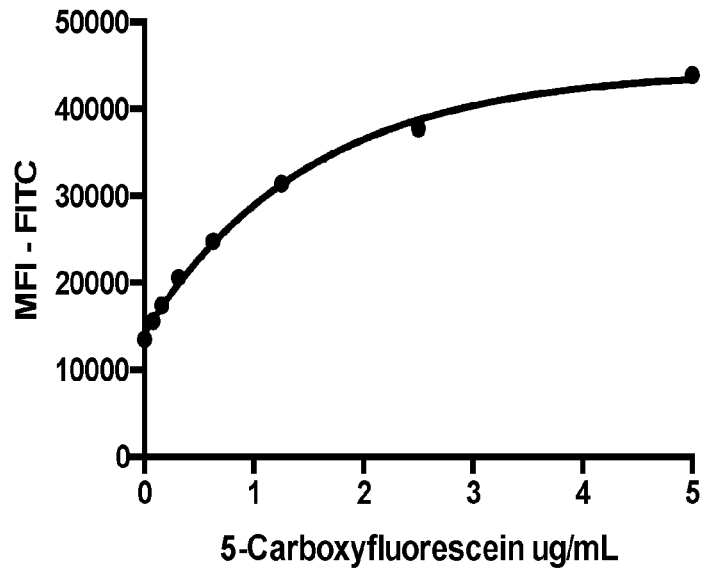
FIG. 1 is a standard curve for 5-carboxyfluorescein in deionised water to determine competitive release of 5-carboxyfluorescein (First Agent) by mouse IgG.

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

As used herein, the term "coordination complex" or "metal complex" or "metal coordination complex" refers to the product of a Lewis acid-base reaction in which neutral molecules or anions (ligands) bond to a central metal atom (or ion) by coordinate covalent bonds. The ligands operate as Lewis bases—they contain at least one pair of electrons to donate to a metal atom/ion. The central metal atoms/ions are Lewis acids—they can accept pairs of electrons from Lewis bases. Preferably, the metal coordination complex is a polymeric metal coordination complex which includes oligomeric metal coordination complexes.

As used herein, the terms "coordinate bond", "coordinately bonded", and like terms, refers to coordinate covalent bonding which is a covalent bond in which one atom (i.e., the donor atom) supplies both electrons. It is considered to be equivalent to the terms "dative covalent bond" and "dipolar bond" and may be used interchangeably herein with these terms.

The term "substrate", as used herein, refers to any substrate on which the metal coordination complex may be coated to thereby provide an activated substrate for further exchange events. In certain embodiments, the substrate may be a particle or other substrate presenting a planar surface or the like. However, in certain embodiments, the substrate is one having internal surfaces. The internal surfaces may be exposed to the external environment, such as with glass and materials comprising synthetic fibres, or the internal surfaces may be substantially enclosed and only open to the external environment through internal pathways or pores, such as with cellulose-based gels and the like. The substrate may therefore be one having internal spaces, pores, paths or voids. Such substrates may include but are not limited to amorphous substrates, matrices and porous materials. The substrates having internal surfaces will be three dimensional materials in terms of their available surfaces for binding as distinct from substrates only presenting exposed outer surfaces for binding such as plates and the like.

The term "internal surface", as used herein, refers to those surfaces of the relevant substrate available for binding and which are within the boundaries or borders of the substrate's external surfaces i.e. they exist within the body of the substrate rather than the outermost external surfaces. The internal surfaces will exist between portions of the substrate material and may be the walls or surfaces forming at least part of the internal spaces, pores, paths or voids described in relation to the term "substrate".

Unless defined otherwise, all technical and scientific terms used herein have the same meaning as would be commonly understood by those of ordinary skill in the art to which this invention belongs.

In one broad form, the invention resides in a method of controlled competitive exchange of a bound first agent and a competing agent including the steps of:
(a) providing a metal coordination complex, having the first agent bound thereto, optionally on a surface of a substrate; and
(b) exposing the metal coordination complex with bound first agent to the competing agent in solution,
to thereby allow the competing agent to exchange with the first agent and become preferentially bound to the metal coordination complex.

According to one aspect of the broad form, there is provided a method of controlled competitive exchange, on a substrate, of a bound first agent and a competing agent including the steps of:
(a) providing a metal coordination complex having one or more ligands bound to the metal of the metal coordination complex;
(b) exposing the metal coordination complex with bound one or more ligands to the first agent, in solution, to thereby have the first agent exchange with the one or more ligands; and
(c) exposing the metal coordination complex with bound first agent, coated on the substrate, to the competing agent in solution,
wherein either the metal coordination complex of step (a) or the metal coordination complex with bound first agent of step (b) is coated onto the substrate, to thereby allow the competing agent to exchange with the first agent and become preferentially bound to the metal coordination complex on the substrate.

The following discussion applies, as appropriate, to all embodiments of the broad form and/or all aspects.

The one or more ligands bound to the metal of the metal coordination complex may be considered to be 'native' or 'pre-formed' ligands in that these are the ligands present at the point of formation of the metal coordination complex from the metal salt. Such native ligands, for example those formed from addition of ethylene diamine or even water molecules present in the complex-forming solution, will, in all aspects of the broad form, be displaced or exchanged for a further molecule such as a first agent. It will be appreciated that the native ligands are small ligands that will be displaced very quickly by most larger molecules or those of greater electron density. They therefore do not allow for a truly controlled exchange reaction with a competing agent. Instead, it has been found that such ligands must first be replaced by the first agent to afford a greater level of control.

The first agents will therefore have a greater mass and/or coordination strength for the metal coordination complex and/or electron density and/or more be complementary to the metal ion or in some other manner display a greater binding preference for the metal of the metal coordination complexes than the native ligands. This, firstly, allows them to displace the native ligands but also allows for greater control in the subsequent exchange reaction with a competing agent. For example, the first agent, in one embodiment, should complement the metal ion. For example, if the metal ion is a hard Lewis acid, such as a chromium metal coordination complex, then a hard Lewis base is preferred. That is, the first agent will be a harder Lewis base than the native or pre-formed ligand when the metal ion is a hard Lewis acid. The converse is also true.

In one preferred embodiment, the metal coordination complex is a polymeric metal coordination complex such as an oligomeric metal coordination complex.

The forming of the oligomeric metal complexes requires a base to form the hydrolytic oligomers so, for example, ethylenediamine when added to the complex-forming mixture will act as an organic base to generate OH groups as well as being a potential ligand itself within the oligomeric metal coordination complex, depending on the pH. Such polymers/oligomers will not readily form if the metal ions are already coordinated to first agents, as defined herein, such as acetate ions. Alternatively, different constructs are formed if the metal ions are already coordinated to first agents, as defined herein, such as delteparin.

Therefore, in forming a polymeric or oligomeric metal complex, the typical native ligands are largely limited to the counter-ions (e.g., CI, Br, $ClO_4$, etc.), water, hydroxides, ethylenediamine or other basic ligands used to form the oligomeric metal coordination complex. Therefore, native ligands are pre-existing ligands on the metal ions or bridging agents (a base) used in the formation of polymeric/oligomeric metal complexes. This means that, in all embodiments described herein, the metal coordination complexes, preferably polymeric metal coordination complexes, will initially be formed with ligands which are not first agents, as defined herein, but which are capable of being competed off or exchanged by such first agents. This is advantageous in that the choice of e.g. the size and electron density of the first agent, as part of a metal coordination complex activated substrate, can be tailored to the specific application the substrate will be employed in and hence be exchanged only for the desired competing agent. Conditions such as molar excess, exposure time and energy (heat) will affect the coordination strength of the first agent and so can be used in the tailoring to suit individual applications.

As such, the first agent, through its relative coordination strength with respect to the competing agent, is an agent that does not change the inherent binding characteristics of the underlying metal coordination complex (for example it does not result in further cross-linking of the coordination complex to form larger polymeric complexes) but rather changes its reaction kinetics for competing and further binding agents. If the first agent, as defined herein, was present during the actual step of formation of the polymeric/oligomeric metal coordination complexes, such metal coordination complexes with the desired coordination potential would not be formed.

It will be appreciated that in forming the metal coordination complex, having the first agent bound thereto, on the surface of the substrate, the first agent is bound substantially on a face of the metal coordination complex opposite that which is bound to the substrate surface.

Suitably, in any embodiment, the step of providing the metal coordination complex having one or more ligands bound to the metal of the metal coordination complex, wherein it is this complex which is coated on to the substrate, may include a step of forming the metal coordination complex having one or more ligands bound to the metal of the metal coordination complex and either subsequently or simultaneously coating it on a surface of the substrate. That is, the metal coordination complex may be formed and then exposed to the substrate or the components of the metal coordination complex may be exposed to the substrate and the metal coordination complex will form and bind on the substrate.

Alternatively, the metal coordination complex of step (a) may first be exposed to the first agent for exchange between the ligands and the first agent, and then the metal coordination complex with bound first agent may be coated onto the substrate.

The nature of the substrate will depend on the intended use and, particularly, whether that use is in vivo or in vitro. For example, in one embodiment, the substrate may be a medical device adapted to be implanted in a human or veterinary patient. Examples of some suitable implantable devices, without limitation thereto, include self-expandable stents, balloon-expandable stents, stent-grafts, grafts (e.g., aortic grafts), artificial heart valves, cerebrospinal fluid shunts, pacemakers, artificial joints, bone plates and implants, drug release devices and matrices and the like. Such substrates are particularly appropriate when the intent is to have a controlled release of a therapeutic from the substrate.

The substrate can also be particles of nano- or micron size dimensions, gels, membranes, plates, tubes, as well as substrates having macro-, meso- or micro-porous structures, etc. that also may be appropriate for use in in vivo or in vitro in a laboratory environment. Particle substrates can be injected into the body to be used as drug delivery vehicles or, alternatively, may be used as components of a column for sample processing and separation. Alternatively, plates or chips, microtubes and the like can be used as substrates for capture and subsequent analysis of analytes when the main purpose of the substrate is the selective sequestration of specific analytes with respect to others in the sample.

Therefore, in one embodiment, the substrate is an implantable medical device or an injectable drug release device.

In one embodiment, the substrate is selected from a metal, a metal alloy, glass and a polymeric substrate.

In one embodiment, the substrate may comprise a metal selected from cobalt, chromium, iron, tantalum, nickel, titanium, platinum, iridium, gold, magnesium and molybdenum.

In one embodiment, the substrate may comprise a metal alloy selected from cobalt and/or chromium alloys, stainless steel, high nitrogen stainless steel, tantalum alloys, nickel-titanium alloys, platinum-iridium alloys, gold alloys and magnesium alloys.

In one embodiment, the substrate comprises a polymeric material which is a hydrophobic polymer. Representative hydrophobic polymers may be selected from the group consisting of PVC, poly(ester amide), polystyrene-poly-isobutylene-polystyrene block copolymer (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (ortho ester), polyphosphazenes, poly (phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(butyl methacrylate), poly(methyl methacrylate), poly(methacrylates), poly(vinyl acetate), poly (ethylene-co-vinyl acetate), poly(ethylene-co-vinyl alcohol), poly(ester urethanes), poly(ether-urethanes), poly (carbonate-urethanes), poly(silicone-urethanes), poly(2-hydroxyethyl methacrylate), PVDF-Solef® (polyvinylidene-fluoride) and poly(urea-urethanes).

In one alternative embodiment, the polymeric material is a hydrophilic polymer. Representative hydrophilic polymers may be selected from the group consisting of polymers and co-polymers of hydroxyethyl methacrylate (HEMA), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, alkoxymethacrylate, alkoxyacrylate, and 3-trimethylsilylpropyl methacrylate (TMSPMA), hydroxy functional poly(vinyl pyrrolidone), polyalkylene oxide, cellulose, nitrocellulose, dextran, dextrin, sodium hyaluronate, hyaluronic acid, elastin and chitosan and cross-linked polymers comprising any two or more of these polymers.

It is an advantage that the oligomeric metal coordination complex can be bonded to a wide variety of metallic and polymeric substrates. This widens the nature of the substrate which can be used in or outside of a patient's body and also allows for ample choice of material when forming a substrate for use in analytical procedures.

By changing the metal salts and reaction environment, it is possible to modulate the binding of the metal coordination complexes to any available electron donating groups on the substrate surface, either prior to or following exchange of the metal coordination ligands with the first agent, and present a coordination layer for binding of the first agent prior (if not already bound) to subsequent competitive exchange or for exposure to a sample comprising both competing agent and further binding agent for selective sequestration.

Where the substrate surface is predominantly hydrophobic with little or no electron donating groups to adequately bind the metal coordination complexes to the substrate, the metal coordination complexes can be modified to improve binding by having one or more co-ordination sites occupied by a hydrophobic ligand for binding the metal coordination complex to the hydrophobic substrate, wherein the hydrophobic ligand binds to the hydrophobic substrate by non-covalent and non-coordinative interactions, and the residual metal coordination sites are available to present a coordination layer to bind the first agent and, subsequently, the competing agent. Such approaches are described in PCT publication WO 2015/192183 in the name of the present applicant, which is herein incorporated by reference in its entirety.

The first agent may be a functional agent selected from the group consisting of therapeutic agents, labelling agents such as fluorescent dyes, steroids, peptides and oligonucleotides. A wide range of such smaller molecules may be appropriate as the first agent as long as the number and binding strength of its ligands for available coordination sites on the metal coordination complex substrate are less than those of the competing agent which will exchange with it.

Therapeutic agents may be selected from a wide range of known therapeutics. Small molecule, drug-like compounds, all commonly have hydrogen bond acceptors and donors based around nitrogen and oxygen atoms. Those having carboxylic acid and other electronegative oxygen species are preferred.

Other smaller molecule first agents may be selected from a wide range of known molecules useful in life science research and/or employed in medical diagnostic and laboratory analytical applications.

In certain embodiments, the first agent may be a nanoparticle as long as the number and binding strength of its ligands are less than that of the competing agent. Examples of such first agents include clusters of therapeutic agents within particles.

In embodiments wherein the desired outcome is the selective sequestration of the competing agent from a sample containing at least one further binding agent, the first agent may be a small organic molecule as described above in the manner of a simple blocking or capping agent. The terms "first agent" and "capping agent" may be used interchangeably herein with "capping agent" generally being used when referring to a first agent which does not itself have therapeutic efficacy i.e. it is a blocking group.

First agents acting as capping agents are those that include nitrogen, oxygen, or sulphur as dative bond forming groups. More preferably, the dative bond forming groups of the capping agent are oxygen or nitrogen. Even more preferably, the capping agent is one comprising a dative bond forming group which is an oxygen containing group. Still even more preferably, the oxygen containing group of the capping agent is selected from the group consisting of sulphates, phosphates, carboxylates, sulphonic acids and phosphonic acids.

In one embodiment, the capping agent may be selected from the group consisting of formate, acetate, propionate, oxalate, malonate, succinate, maleate, sulphate, phosphate, and hydroxyacetate.

In certain embodiments, the capping agent is a monodentate or bidentate capping agent.

The first agent/capping agent will have a greater molecular mass and/or greater coordination strength for the metal coordination complex and/or greater electron density and/or greater number of ligand binding sites than the native or pre-formed ligand it is to displace. In one embodiment, the capping agent must better complement the metal ion of the metal coordination complex. If the metal ion is a hard Lewis acid, then it is preferred that the capping agent is a harder Lewis base than the native or pre-formed ligand, and vice versa.

In embodiments, the capping agent has a molecular mass of less than 1000 Daltons, or less than 500 Daltons, or less than 400 Daltons, or less than 300 Daltons. Any of these values may be combined with a lower value of 10, 30 or 50 Daltons to form a range of molecular mass values for the capping agent such as 10 to 1000, 10 to 500, 10 to 400 or 10 to 300 Daltons.

The first agent/capping agent, by its nature, sets a threshold level above which its coordination strength will not be strong enough to resist the exchange and binding, via avidity bonding, of a larger competing agent such as a protein or fragment thereof. However, in the presence of other small molecules within the sample, such as for example other further binding agents, the threshold coordination strength of the first agent/capping agent is such that the further binding agents may not be sufficiently strong enough to compete. It will be understood that even if the further binding agent is a larger organic molecule with multiple electron donating sites, such as a carbohydrate or a steroid, and the first agent is a simple capping agent, such as an acetate capping group, then even if there is some small degree of exchange between the acetate and the carbohydrate or steroid it will be significantly less than the exchange between the acetate group and the protein-based agent.

Further, even in the event that a small amount of carbohydrate or steroid or other further binding agent becomes bound to the oligomeric metal coordination complex then the protein-based competing agent will exchange with that so that, within the analytical or therapeutic time frame, the overall effect of the process is the selective sequestration or competitive exchange between first agent/capping agent and competing agent. To be clear, such small amounts of temporary binding of any further binding agent prior to completion of the exchange reaction with the competing agent are considered to be within the terms of the method of competitive exchange and selective sequestration as defined herein.

In one embodiment of the first aspect, the competing agent has a greater molecular mass and/or number of electron donating sites and/or coordination strength for the metal coordination complex than each (i.e. separately) of the first agent and the further binding agent.

In certain embodiments, the first agent has a molecular mass of less than 20,000 Daltons, or less than 10,000 Daltons or less than 5,000 Daltons, or less than 1000 Daltons, and in another embodiment, the first agent has a molecular mass of less than 750 or 500 Daltons. Any of these values may be coupled with a lower molecular mass value of 20, 30 or 50 Daltons to form a molecular mass range such as 20 to 20,000, 20 to 10,000, 20 to 5,000, 20 to 1000, 20 to 750 or 20 to 500 Daltons. As a consequence of their size, smaller molecules will have significantly less potential to coordinate with metal coordination complexes when compared to macromolecules having greater potential for avidity binding.

In certain embodiments, the molecular mass ratio of competing agent to first agent is greater than about 10:1, preferably greater than about 100:1, more preferably greater than about 1,000:1, even more preferably greater than about 10,000:1.

In another embodiment, and by way of an example, if the coordination moiety of the first agent is a carboxylate group, then either the molar concentration of the competing agent and/or the molar concentration of carboxylate groups (such as aspartic and glutamic acids) must be in excess. In certain embodiments, the molar ratio of coordination ligands on the competing agent to those on the first agent is greater than about 10:1, preferably greater than about 100:1, more preferably greater than about 1,000:1, and even more preferably greater than about 10,000:1.

Therefore, in one embodiment, the first agent has a lower molecular weight and/or lower coordination strength for the metal coordination complex and/or fewer electron-donating sites and/or is less complimentary to the metal coordination complex than the competing agent. Because different ligands acting as the first agent can have different coordination strengths to the metal ion, and the conditions of binding such as time and temperature can also affect coordination strength, molecular mass is not the single determinate of desired competition but the overall relationship or ratio between coordination strength of the first agent (whose coordination strength can be tuned or further adjusted) and the coordination strength of the competing agent (whose coordination strength is its avidity to compete with first agent).

In certain embodiments, the first agent is a small drug-like molecule and the competing agent is a protein or protein fragment.

In another embodiment, the first agent can be a larger molecule such as heparin and similar polymeric and oligomeric agents and the competing agent is a protein or a larger complex such as a cell.

As previously stated, the competing agent will have a greater number of electron donating sites or greater coordination strength for the metal coordination complex than the bound first agent. This results in the competing agent having a greater avidity for the oligomeric metal coordination complex than the bound first agent and so, over time, the competing agent will compete with the first agent and eventually drive it off the oligomeric metal coordination complex. In this respect, relative molecular sizes of first agent and competing agent can be a useful, although not sole, important indicator of relative competition between the agents. The difference in avidity between the first agent and the competing agent can be used to select the appropriate level of first agent coordination strength to thereby provide the requisite level of control over the competitive exchange reaction.

In preferred embodiments, the competing agent is a large biomolecule such as a protein or a fraction thereof, or a larger protein or protein complex and other biomolecule complexes such as viruses or cells.

The competing agent may have a molecular mass of greater than 20,000 Daltons, or greater than 50,000 Daltons, greater than 100,000 Daltons or greater than 200,000 Daltons. Where the competing agent is a discrete macromolecule, the competing agent may have a molecular mass of between 20,000 to 1,000,000 Daltons, 20,000 to 750,000 Daltons, 20,000 to 500,000 Daltons, 20,000 to 300,000 Daltons, 50,000 to 1,000,000 Daltons, 50,000 to 750,000 Daltons, 50,000 to 500,000 Daltons, 50,000 to 300,000 Daltons, 100,000 to 1,000,000 Daltons, 100,000 to 750,000 Daltons, 100,000 to 500,000 Daltons or 100,000 to 300,000 Daltons.

Biomolecules, such as proteins, typically have a far greater molecular mass and multiple electron-donating sites over a surface area, when compared with typical drug like or other therapeutic molecules which may form the first agent. Once such large biomolecules bind at one coordination site, the local molar concentration of its neighbouring electron donating sites to compete for metal coordination on a substrate is far higher than any small first agent. This results in them having a greater propensity to bind to the oligomeric metal coordination complex and so they will compete the first agent off resulting in an exchange between the two agents on the oligomeric metal coordination complex.

It will be appreciated that if the substrate with the oligomeric metal coordination complex and bound first agent is implanted or injected into a patient's body then the competing agent will in fact be a number of different biomolecules which are naturally occurring.

It is a significant advantage of the present invention that the oligomeric metal coordination complex provides a surface which displays selectivity for agents with a greater potential for avidity bonding. That is, the competing agent naturally has a greater affinity for binding thereto and after exchanging with the first agent is directly bonded to the oligomeric metal coordination complex through multiple interactions the accumulated strength of which results in anchoring of the competing agent to the oligomeric metal coordination complex as if it were bonded via standard covalent bonding. The bonding will involve at least one coordinate (dative) covalent bond and in certain embodiments the majority of the bonding strength is provided by coordinate bonds. The competing agent will not, to any significant extent in terms of number of molecules, be exchanged thereafter with the first agent as the first agent does not have sufficient electron donating sites or coordination strength to compete off the competing agent. However, it will be appreciated that if the oligomeric metal coordination complex with bound competing agent is exposed to a further, different, competing agent which has greater electron donating potential then it may be exchanged, as was the case for the first agent.

Therefore in one embodiment of any of the aspects, the metal coordination complex with bound competing agent may be exposed to a second and/or third and/or fourth competing agent with said competing agents each being selected to have a greater molecular mass and/or electron density and/or avidity for the metal coordination complex than the currently bound competing agent.

Further, if it is desired to release a therapeutic molecule (first agent) from the oligomeric metal coordination complex and the competing agent is to be a range of native proteins and other biomolecules occurring within the patient's body then, even though the nature of the competing agent cannot be tightly controlled it is still possible to tailor the rate of release of the drug. Where the therapeutic molecule lacks sufficient coordination potential to resist exchange to the extent desired, one approach to this end is to 'tag' the drug-like molecule (first agent) with coordinating ligands or fragments thereof to increase its overall mass as well as the number of electron donating sites it possesses. This effectively increases the affinity of the drug-like molecule for the oligomeric metal coordination complex and so it will take a greater time period for it to exchange with the native competing agents thereby providing for a slower release rate and greater duration of release. The greater the mass and electron donating potential of the tag the slower will be the exchange rate and so the choice of tag provides an element of fine control. This is an important advantage in the competitive exchange process provided for by the present method.

The tag and the site of its attachment to the first agent, for example the drug-like molecule, will be chosen such that the activity of the drug, upon its release, is not negatively affected. Such modification of therapeutics with linkers and further coordination potential is within the skill of one in the art.

In one embodiment, the tag may be selected from those that include nitrogen, oxygen, or sulphur as dative bond forming groups. More preferably, the dative bond forming groups are oxygen or nitrogen. Even more preferably, the dative bond forming group is an oxygen containing group. Still even more preferably, the oxygen containing group is selected from the group consisting of oxides, hydroxides, water, sulphates, phosphates, carboxylates, sulphonic acids, phosphonic acids, and the like.

In another embodiment, the oligomeric metal coordination complex and the drug molecule can be mixed together with hydrophilic polymers to form a cluster of therapeutic agents within a matrix of hydrophilic polymers. Such clusters can themselves be bound to an oligomeric metal coordination complex on the substrate surface to thereby allow;

(a) Competition with competing agent at the substrate as previously described; and
(b) Competition with competing agent at the hydrophilic polymer cluster level.

to thereby allow competition and exchange between the agents at two levels. By such methods, multiple levels of competition between the agents can be achieved to control the rate of exchange over the whole system.

In a further embodiment, the method may be considered to be a method of sequestration of the competing agent.

In this embodiment, competing agent may be present in a sample along with at least one further binding agent.

Therefore, in one aspect, there is provided a method of selective sequestration of a competing agent, onto a substrate, from a sample in the presence of a further binding agent including the steps of:

(a) providing a metal coordination complex having one or more ligands bound to the metal of the metal coordination complex, on a surface of the substrate; and
(b) exposing the metal coordination complex with bound one or more ligands to a first agent, in solution, to thereby have the first agent exchange with the one or more ligands; and
(c) exposing the metal coordination complex with bound first agent, coated on the substrate, to the sample comprising the competing agent and the further binding agent, wherein either the metal coordination complex of step (a) or the metal coordination complex with bound first agent of step (b) is coated onto the substrate and wherein the competing agent has a greater number of electron donating sites than each of the first agent and the further binding agent, to thereby allow the competing agent to preferentially exchange with the first agent and become preferentially bound to the metal coordination complex.

As previously described, the greater the degree of bonding of any agent to the polymeric/oligomeric metal coordination complex then the more time will be required to have it exchange with a competing agent. The time for the exchange will also be affected, in part, by the nature of the competing agent and the number of electron donating sites it has as well as its mass. It will be appreciated then that this provides for a significant level of control over the exchange process, which has not been described or envisaged in the prior art, allowing tailoring of the rate of release based on the natures of both the first agent and competing agent and also the nature of the oligomeric metal coordination complex itself. Such flexibility is a significant advantage of the present invention.

The method of selective sequestration of the competing agent may also be considered to be a selective enrichment of compounds or biomolecules which are left remaining within the sample after binding of the competing agent to the oligomeric metal coordination complex. For example, there is a need for simple, quick methods for enrichment to allow subsequent identification of lower molecular weight fractions in the presence of highly abundant proteins. In another example, it is often desirable to remove interfering proteins from the sample when running analytical tests, such as in the detection of various steroids. The present invention allows for the provision of a substrate, which may be a chip, column or like collection template, on which the oligomeric metal coordination complex is formed to be contacted with the biological sample. It will be appreciated that although molecular weight is not the single criteria for competition between agents, it is a good approximation for the relative number of coordinating ligands presented by the agent. As discussed, it is expected that there will be some degree of initial coordination with the first agent but this would soon be exchanged off the oligomeric metal coordination complex by the larger molecular weight proteins in the sample due to their greater mass and number of electron donating sites.

In this embodiment, it is important that the availability of metal coordination complexes on the substrate is limiting with respect to at least the amount of the first agent to thereby allow for competition of the various agents to occur. In this way, according to the relative amounts of the metal coordination complex on the substrate, the agents, pH, temperature and time, it is possible to achieve a useful degree of control over the competitive exchange process and the final outcome. Therefore in one embodiment, the method of any aspect includes the step of controlling one or more of the pH, temperature or time span of the exchange reaction.

This provides for a rapid, efficient and relatively cheap means of enriching lower molecular weight fractions from the biological sample.

In an alternative aspect of the broad form, the method may be a method of generating a binding layer on an internal surface of a substrate, this method including the steps of:
(a) providing a metal coordination complex having one or more ligands bound to the metal of the metal coordination complex;
(b) exposing the metal coordination complex with bound one or more ligands to a first agent, in solution, to thereby have the first agent exchange with the one or more ligands and become coordinately bonded to the metal; and
(c) coating the metal coordination complex having bound first agent onto the internal surface of the substrate, to thereby generate the binding layer on the internal surface of the substrate.

In this aspect only the internal surface of the substrate may be considered to be the competing agent. This is because the metal coordination complex with first agents/capping groups bound on multiple coordination sites on the metal oligomer experiences competition from the substrate surface which is effectively acting as a very large biomolecule, in the case of nitrocellulose or similar substrates. The result is that the level of competition means the metal coordination complex becomes bound to the substrate surface with the first agents/capping agents having been exchanged but remaining on the face of the metal coordination complex extending into the internal pores or spaces of the substrate. These remaining first agents/capping agents are therefore available for further exchange by a second competing agent such as a capture molecule, target molecule or the like.

Therefore, in one embodiment, step (c) may be a step of coating the metal coordination complex having bound first agent onto the internal surface of the substrate to thereby allow the substrate, as a competing agent, to preferentially exchange with the first agent on one surface of the metal coordination complex and have the metal coordination complex become preferentially bound thereto.

The ligands bound to the metal of the metal coordination complex may be native ligands as discussed previously. Such native ligands may be monodentate ligands.

In this aspect, the first agent/capping agent may be as previously defined.

Further to the above, according to one aspect of the broad form, there is provided a method of capturing a competing agent on an internal surface of a substrate including the steps of:
(a) providing a substrate comprising an internal surface, the internal surface at least partially coated with a metal coordination complex having a bound first agent; and
(b) exposing the coated substrate with bound first agent to the competing agent in solution, to thereby allow the competing agent to preferentially exchange with the first agent and become preferentially bound to the metal coordination complex, to thereby capture the competing agent on the internal surface of the substrate.

The coated substrate with bound first agent may be formed as described above for the method of generating a binding layer on an internal surface of a substrate and so the method may include each of those steps, as required.

When the substrate is considered to have acted as a competing agent in the formation of the internal surface at least partially coated with a metal coordination complex having a bound first agent then step (b) may be considered to be exposure to a second or further competing agent. This second or further competing agent may be as previously defined for the competing agent of any aspect described herein.

It will therefore be appreciated that this aspect relies on use of the substrate with a binding layer generated on an internal surface thereof, as described in the above aspect. This aspect may therefore incorporate the steps of that previous aspect including the (i) providing of a metal coordination complex having one or more ligands bound to the metal of the metal coordination complex; (ii) the exposing of the metal coordination complex with bound one or more ligands to a first agent, in solution, to thereby have the first agent exchange with the one or more ligands and become coordinately bonded to the metal; and (iii) the coating of the metal coordination complex having bound first agent onto the internal surface of the substrate.

The competing agent to be captured may be a target molecule.

In one embodiment, wherein the competing agent to be captured is a target molecule, the method may further include the step (a)(i) of exposing the coated substrate of step (a) to a capture molecule to displace the first agent and coordinately bond to the metal coordination complex, the capture molecule being capable of binding the target molecule.

According to a further aspect of the invention, there is provided a substrate having an internal surface comprising a binding layer, the binding layer comprising a metal coordination complex having a first agent coordinately bonded thereto.

The substrate with the internal surface comprising the binding layer may be formed as described above for the method of generating a binding layer on an internal surface of a substrate.

The capture molecule is adapted to bind the target molecule.

The metal coordination complex is preferably a polymeric or an oligomeric metal coordination complex as previously described.

The internal surface of the substrate may be substantially coated with the metal coordination complex having bound first agent.

The substrate for these aspects may be any substrate having internal spaces, pores, paths or voids which themselves present or form at least part of an internal surface available for binding of the metal coordination complex.

The substrate for this embodiment may be selected from an amorphous material, a matrix and a porous material, each of which will present internal surfaces.

In one embodiment, the substrate is selected from a metal substrate, a glass substrate and a polymeric substrate.

When the substrate having the internal surface is polymeric it may be any porous plastic, such as synthetic High Density Polyethylene (HDPE), including membranes and gels produced from synthetic or biological polymers.

In certain embodiments, the substrate having the internal surface may be any membrane or other materials which are appropriate for use as lateral flow strips. These will typically be of the kind used for immobilising capture molecules such as antibodies on the capture line bound by the present activated metal complexes on the membrane. It has been found that such porous membranes can be activated as described herein without significantly negatively affecting porosity and solvent flow through those activated regions as well as the rest of the membrane. In contrast, without use of a capping/first agent, the addition of metal complexes can lead to uncontrolled cross-linking thereby significantly negatively affecting porosity and solvent flow.

In one embodiment, the substrate having the internal surface may be a cellulose substrate, preferably a nitrocellulose substrate.

Alternatively, the substrate having the internal surface may be one of a number of other components used in lateral flow strips such as glass fibres, cellulose, polyester, rayon, and similar materials.

In other embodiments, the substrate having the internal surface may be cellulose esters of various kinds such as acetates and propionates, cellulose nitrates and sulphates; cellulose ethers such as methyl and ethylcellulose; and other cellulose based derivatives.

Further substrates having the internal surface may include polysaccharides and other biological materials such as cotton, hemp, abaca, etc. made into fibres, filters, paper and other membrane-type materials.

In other embodiments, the substrate having the internal surface may be synthetic materials such as such as nylon, acrylic, polyesters, made into fibres, filters, paper and other membrane type materials.

In other embodiments, the substrate having the internal surface may exist as a foam such as polystyrene, urea-formaldehyde, polyurethane, phenolic resin foams.

The internal surface of the substrate may be one or more walls defining a flow path, pore or void or may be the surfaces of the substrate material when separated by internal spaces such as would be observed with materials formed of fibres. The space, flow path, pore or void will be of sufficient diameter to allow the passage therethrough of antibodies, antigens and the like biomolecules. Alternatively, the space, flow path, pore or void maybe part of a filtration process to remove unwanted materials in air, waste water, oils and any other liquid where there is a need to capture and remove or sequester some target molecule.

In one embodiment of these aspects, the first agent is a capping agent which is non-functional, as previously described. This means that it simply acts as a controllable leaving group to modify or temporarily suppress reactivity over the whole oligomeric metal coordination complex, or of some coordination sites within the oligomeric metal complex, for the purpose of binding to the internal surface of the porous substrate while preventing cross-linking with itself and then allowing subsequent binding of synthetic and/or biological materials to the binding layer.

In certain embodiments, the capping agent is a monodentate or bidentate capping agent.

In embodiments, the capping agent has a molecular mass as previously defined.

The capping agent is bound to the metal coordination complex following the formation of the oligomeric metal coordination complex.

The target molecule may be any molecule that is capable of forming a complex or conjugate with the metal coordination complex or capture molecule. Non-limiting examples of target molecules include proteins inclusive of antibodies or antibody fragments, peptides, enzymes, epitopes and other antigens, antigen receptors, hormone receptors, growth factor receptors, cytokine receptors, hormones, growth factors or cytokines, small molecules, cells and cellular fractions, organelles or other components thereof, biological markers such as cell surface markers, nucleic acids such as single- or double stranded DNA and RNA, and derivatives, cooligomers and any fragments or combinations thereof. Small molecules, ions, carbohydrates, whole cells, bacteria, viruses, fungi and the like may also be representative of the target molecule. The target molecule may further be any unwanted materials in air, waste water, oils and any other liquid where there is a need to capture and remove or sequester the target molecule.

The target molecule may be a component of a sample to which the substrate comprising the binding layer is exposed.

The sample may be an industrial waste sample or a biological sample.

In certain embodiments of the aforementioned aspects, the capture molecule, when required, may be any molecule that is capable of forming a complex or conjugate with the metal coordination complex and the target molecule. Non-limiting examples of the capture molecule include carbohydrates, bacteria, viruses, fungi as well as proteins inclusive of antibodies or antibody fragments, peptides, enzymes, epitopes and other antigens, antigen receptors, hormone receptors, growth factor receptors, cytokine receptors, hormones, growth factors or cytokines, cells and cellular fractions, organelles or other components thereof, biological markers such as cell surface markers, nucleic acids such as single- or double stranded DNA and RNA, and derivatives, cooligomers and any fragments or combinations thereof.

It will therefore be appreciated that the capture molecule and the target molecule may be "complementary binding partners". By this is meant, for example, an antibody and antigen (e.g. an epitope), whereby the antigen or epitope may be the target molecule and the antibody or antibody fragment may be the capture molecule, or vice versa. It will also be apparent to a skilled person that complementary binding partners could include complementary DNA strands, growth factors and growth factor receptors and enzymes and substrates, although without limitation thereto.

Therefore, in some embodiments of, the target molecule may bind directly to the metal coordination complex binding layer. In alternative embodiments, it may bind to a further agent, such as the capture molecule, which has first become bound to the metal coordination complex.

Accordingly, the coated substrate may be useful for detecting target molecules in samples such as biological samples, diagnostic samples, food samples, air samples, water samples and the like. Non-limiting examples of biological and/or diagnostic samples include tissue, organ and tumour biopsies, body fluids such as urine, blood, serum, cerebrospinal fluid, semen, tears and sputum, although without limitation thereto.

In any of the embodiments described herein, the first agent/capping agent is bonded directly to the oligomeric metal coordination complex through one or more coordinate bonds.

In one embodiment, the oligomeric metal coordination complex comprises a metal ion selected from the group consisting of chromium, ruthenium, iron, cobalt, aluminium, zirconium and rhodium.

In one embodiment, the metal is chromium.

The metal ion may be present in any applicable oxidation state. For example, chromium is known to have the following oxidation states of I, II, III, IV, V, or VI. In an embodiment in which the metal ion is a chromium ion, it is preferred that the chromium has an oxidation state of III.

In certain embodiments, mixtures of different metal ions may be used, for example, to form a plurality of different metal coordination complexes to make up the oligomeric metal coordination complex. In such cases, it is preferred that at least one metal ion is chromium.

Metals are known to form a range of metal coordination complexes. In one embodiment, the oligomeric metal coordination complex comprises a ligand forming the complex with the metal. Ligands for forming the oligomeric metal coordination complex are those that include nitrogen, oxygen, or sulphur as dative bond forming groups. More preferably, the dative bond forming groups are oxygen or nitrogen. Even more preferably, the dative bond forming group is an oxygen containing group. Still even more preferably, the oxygen containing group is selected from the group consisting of oxides, hydroxides, water, sulphates, phosphates, or carboxylates.

In an embodiment, the ligand is a mono-, di-, or tri-atomic ligand. Preferably, the ligand is an oxygen containing species such as an oxide, a hydroxide, or water; wherein the dative bond forming group is oxygen.

In one embodiment the ligand is an inorganic ligand. Preferably the ligand is an oxo ligand.

The layer of oligomeric metal coordination complex is stabilised, in part, by cross-linking of the metal ions with each other to form the larger oligomeric metal-ligand complexes. This results in the oligomeric metal coordination complex being stable not only to conditions prevalent in the body but also to physical processes, such as sterilisation, to which the substrate may be subjected depending on its ultimate use.

In one embodiment, the ligand is a bridging compound that is datively bonded to at least two of the metal ions. Preferably, this results in the formation of the oligomeric metal-ligand complex.

In one exemplary embodiment, the metal coordination complex is an oxo-bridged chromium (III) complex. This complex may optionally be further oligomerised with one or more bridging couplings such as carboxylic acids, sulphates, phosphates and other multi-dentate ligands.

In any of the embodiments described herein, the first agent and competing agent are, when bound, bonded directly to the oligomeric metal coordination complex through one or more coordinate bonds.

In preparing to form the oligomeric metal coordination complex the metal ion which will be a component of the oligomeric metal coordination complex may be associated with a counter-ion (such as an anion selected from the group consisting of chloride, acetate, bromide, nitrate, perchlorate, alum, fluoride, formate and sulphate), which can be co-ordinating or non-coordinating. In one embodiment the counter-ion is a non-coordinating anion. In another embodiment the counter-ion is a coordinating anion.

The metal-ligand complexes which form the oligomeric metal coordination complex can generally be formed by providing conditions for forming electron donating groups for bridging or otherwise linking or bonding two or more metal ions. This can be done by providing a pH below pH 7, preferably about 1.5 to 6, preferably about 2 to 5.5 to the composition formed from the contact of the metal-ligand complexes with the surface of the active material.

Various chromium salts such as chromium chloride, chromium nitrate, chromium sulphate, chromium perchlorates, may be used to form the metal-ligand complex. These salts are mixed with an alkaline solution, such as potassium hydroxide, sodium bicarbonate, sodium sulphite and ammonia to form different metal-ligand complexes. Organic reagents that can act as bases such as ethylene diamine, bis(3-aminopropyl)diethylamine, pyridine, imidazoles, can also be used. The size and structure of the metal-ligand complex can vary with pH, temperature, solvents and other conditions.

The metal-ligand complex is further stabilised by cross-linking the metal ions with each other to form larger oligomeric metal coordination complex. Such oligomeric metal coordination complexes can be pre-formed and applied to the substrate, or formed in-situ on the substrate. In this case, the ligands are able to form multiple dative bonds with multiple metal ions, to effectively bridge or cross-link the metal ions. That is, the ligand may form dative bonds with two or more metal ions, thereby linking one metal ion to another metal ion.

Exemplary oxo-bridged chromium structures are provided below:

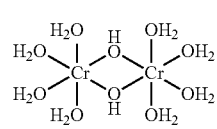

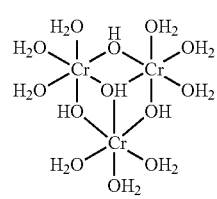

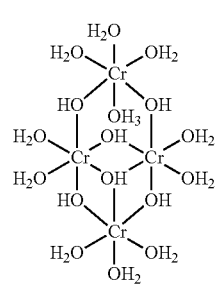

On application to the substrate, at least one of the water or hydroxyl groups on each of the metal-ligand complexes is replaced by a dative bond with the surface of the substrate. This is illustrated below wherein "X" represents the dative bond to the substrate.

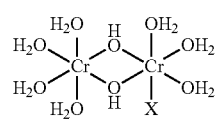

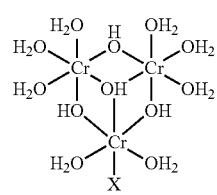

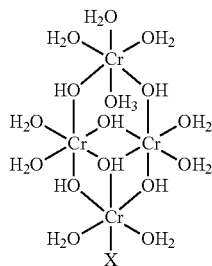

It will also be appreciated that multiple water or hydroxyl groups may be replaced by a dative bond with the substrate, for example each chromium ion may form a dative bond with the substrate surface.

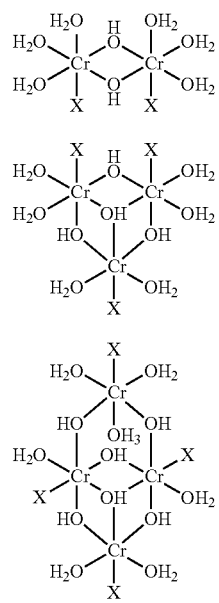

In addition, the water and/or hydroxyl groups may be replaced by a dative bond with another component of the coating, such as with a polyanionic non-functional molecule.

The various features and embodiments of the present invention, referred to in individual sections above apply, as appropriate, to other sections, mutatis mutandis. Consequently features specified in one section may be combined with features specified in other sections as appropriate.

ITEMIZED LISTING OF EMBODIMENTS

1. A method of controlled competitive exchange of a bound first agent and a competing agent including the steps of:
 (a) providing a metal coordination complex, having the first agent bound thereto, optionally on a surface of the substrate; and
 (b) exposing the metal coordination complex with bound first agent to the competing agent in solution,
 to thereby allow the competing agent to exchange with the first agent and become preferentially bound to the metal coordination complex.

2. A method of controlled competitive exchange, on a substrate, of a bound first agent and a competing agent including the steps of:
 (a) providing a metal coordination complex having one or more ligands bound to the metal of the metal coordination complex;
 (b) exposing the metal coordination complex with bound one or more ligands to the first agent, in solution, to thereby have the first agent exchange with the one or more ligands; and
 (c) exposing the metal coordination complex with bound first agent, coated on the substrate, to the competing agent in solution,
 wherein either the metal coordination complex of step (a) or the metal coordination complex with bound first agent of step (b) is coated onto the substrate, to thereby allow the competing agent to exchange with the first agent and become preferentially bound to the metal coordination complex on the substrate.

3. A method of selective sequestration of a competing agent, onto a substrate, from a sample in the presence of a further binding agent including the steps of:
 (a) providing a metal coordination complex having one or more ligands bound to the metal of the metal coordination complex;
 (b) exposing the metal coordination complex with bound one or more ligands to a first agent, in solution, to thereby have the first agent exchange with the one or more ligands; and
 (c) exposing the metal coordination complex with bound first agent, coated on the substrate, to the sample comprising the competing agent and the further binding agent,
 wherein either the metal coordination complex of step (a) or the metal coordination complex with bound first agent of step (b) is coated onto the substrate and wherein the competing agent has a greater number of electron donating sites than each of the first agent and the further binding agent, to thereby allow the competing agent to preferentially exchange with the first agent and become preferentially bound to the metal coordination complex.

4. A method of generating a binding layer on an internal surface of a substrate, this method including the steps of:
 (a) providing a metal coordination complex having one or more ligands bound to the metal of the metal coordination complex;
 (b) exposing the metal coordination complex with bound one or more ligands to a first agent, in solution, to thereby have the first agent exchange with the one or more ligands and become coordinately bonded to the metal; and
 (c) coating the metal coordination complex having bound first agent onto the internal surface of the substrate,
 to thereby generate the binding layer on the internal surface of the substrate.

5. A method of altering or manipulating the binding kinetics, wettability or other surface properties of a metal coordination complex coated substrate including the steps of:
 (a) providing a substrate at least partially coated with a metal coordination complex having one or more ligands bound to the metal of the metal coordination complex;
 (b) exposing the metal coordination complex with bound one or more ligands to the first agent, in solution, to thereby have the first agent exchange with the one or more ligands,
 to thereby alter or manipulate the binding kinetics, wettability or other surface properties of the metal coordination complex coated substrate.

6. A method of capturing a competing agent on an internal surface of a substrate including the steps of:
  (a) providing a substrate comprising an internal surface, the internal surface at least partially coated with a metal coordination complex having a bound first agent; and
  (b) exposing the coated substrate with bound first agent to the competing agent in solution,
  to thereby allow the competing agent to preferentially exchange with the first agent and become preferentially bound to the metal coordination complex to thereby capture the competing agent on the internal surface of the substrate.

7. A substrate having an internal surface comprising a binding layer, the binding layer comprising a metal coordination complex having a first agent coordinately bonded thereto.

8. The method or substrate of any of the preceding items wherein the first agent is different from the ligand having been attached to the metal coordination complex at the point of its having been formed from the metal salt.

9. The method or substrate of any of the preceding items wherein the first agent is not a group or ligand having been attached to the metal coordination complex at the point of its having been formed from the metal salt.

10. The method or substrate of any of the preceding items wherein the first agent has a greater molecular mass, and/or coordination strength for the metal coordination complex, and/or electron density and/or number of electron donating groups and/or avidity or in some other manner a greater binding preference for the metal of the metal coordination complex than the ligand having been attached to the metal coordination complex at the point of its having been formed from the metal salt.

11. The method or substrate of any of the preceding items wherein the ligand having been attached to the metal coordination complex at the point of its having been formed from the metal salt are monodentate ligands.

12. The method or substrate of any of the preceding items wherein the metal coordination complex may first be exposed to the first agent for exchange between the ligands having been attached to the metal coordination complex at the point of its having been formed from the metal salt and the first agent, and then the metal coordination complex with bound first agent may be coated onto the substrate.

13. The method or substrate of any of the preceding items wherein the metal coordination complex may first be bound to the substrate before being exposed to the first agent for exchange between the ligands having been attached to the metal coordination complex at the point of its having been formed from the metal salt and the first agent.

14. The method or substrate of any of the preceding items wherein the substrate is selected from a metal, a metal alloy, glass and a polymer.

15. The method or substrate of any of the preceding items wherein the substrate comprises a metal selected from cobalt, chromium, iron, tantalum, nickel, titanium, platinum, iridium, gold, magnesium and molybdenum.

16. The method or substrate of any of the preceding items wherein the substrate comprises a metal alloy selected from cobalt and/or chromium alloys, stainless steel, high nitrogen stainless steel, tantalum alloys, nickel-titanium alloys, platinum-iridium alloys, gold alloys and magnesium alloys.

17. The method or substrate of any of the preceding items wherein the first agent is a functional agent selected from the group consisting of therapeutic agents, labelling agents such as fluorescent dyes, steroids, peptides and oligonucleotides.

18. The method or substrate of any of the preceding items wherein the molecular mass, and/or coordination strength for the metal coordination complex, and/or electron density, and/or number of electron donating groups of the first agent are fewer/less than those of the competing agent.

19. The method or substrate of any of the preceding items wherein the first agent is a capping agent which comprises nitrogen, oxygen, or sulphur as a dative bond forming group.

20. The method or substrate of any of the preceding items wherein the dative bond forming groups of the first agent/capping agent are oxygen or nitrogen.

21. The method or substrate of any of the preceding items wherein the first agent/capping agent is one comprising a dative bond forming group which is an oxygen containing group.

22. The method or substrate of item 21 wherein the oxygen containing group of the first agent/capping agent is selected from the group consisting of sulphates, phosphates, carboxylates, sulphonic acids and phosphonic acids.

23. The method or substrate of any of the preceding items wherein the first agent/capping agent is selected from the group consisting of formate, acetate, propionate, oxalate, malonate, succinate, maleate, sulphate, phosphate, and hydroxyacetate.

24. The method or substrate of any of the preceding items wherein the first agent/capping agent is a monodentate or bidentate capping agent.

25. The method or substrate of any of the preceding items wherein the first agent/capping agent has a molecular mass of less than 20,000 Daltons, or less than 10,000 Daltons, or less than 5,000 Daltons, or less than 1,000 Daltons, and in another embodiment, the first agent has a molecular mass of less than 750 or 500 Daltons and any of these values may be coupled with a lower molecular mass value of 20, 30 or 50 Daltons to form a molecular mass range such as 20 to 5000, 20 to 1000, 20 to 750 or 20 to 500 Daltons.

26. The method or substrate of any of the preceding items wherein the molecular mass ratio of competing agent to first agent is greater than about 10:1, preferably greater than 100:1, more preferably greater than about 1,000:1, even more preferably greater than about 10,000:1.

27. The method or substrate of any of the preceding items wherein the molar ratio of coordination ligands on the competing agent to those on the first agent is greater than about 10:1, preferably greater than about 100:1, more preferably greater than about 1,000:1, and even more preferably greater than about 10,000:1.

28. The method or substrate of any of the preceding items wherein the first agent is a small drug-like molecule and the competing agent is a protein or protein fragment.

29. The method or substrate of any of the preceding items wherein the competing agent has a molecular mass of greater than 20,000 Daltons, or greater than 50,000 Daltons, greater than 100,000 Daltons or greater than 200,000 Daltons 30. The method or substrate of any of the preceding items wherein the first agent is modified with a tag to increase its molecular weight and/or electron-donating capacity.

31. The method or substrate of any of the preceding items wherein when the competing agent to be captured is a target molecule, the method may further include the step (a)(i) of exposing the coated substrate of step (a) to a capture molecule to displace the first agent/capping agent and coordinately bond to the metal coordination complex, the capture molecule being capable of binding the target molecule.

32. The method or substrate of any of the preceding items wherein the metal coordination complex is an oligomeric metal coordination complex.

33. The method or substrate of any of the preceding items wherein the metal coordination complex comprises a metal ion selected from the group consisting of chromium, ruthenium, iron, cobalt, aluminium, zirconium and rhodium.

34. The method or substrate of any of the preceding items wherein the metal of the metal coordination complex is chromium.

35. The method or substrate of any of the preceding items wherein the metal ion may be present in any applicable oxidation state but when the metal is chromium it is preferred that the chromium has an oxidation state of III.

36. The method or substrate of any of the preceding items wherein the ligand bonded to the metal coordination complex at its point of formation (the native ligand) are those that include nitrogen, oxygen, or sulphur as dative bond forming groups.

37. The method or substrate of any of the preceding items wherein the ligand bonded to the metal coordination complex at its point of formation (the native ligand) is an oxygen containing group selected from the group consisting of oxides, hydroxides, water, sulphates, phosphates, or carboxylates.

38. The method or substrate of any of the preceding items wherein the ligand bonded to the metal coordination complex at its point of formation (the native ligand) is an oxo ligand.

39. The method or substrate of any of the preceding items wherein the metal coordination complex is an oxo-bridged chromium (III) complex.

The following examples are provided by way of illustration and are in no way limiting upon the scope of the invention.

Experimental

Example 1: Preparation of Metal-Ligand Coordination Complex Solutions

Three different solutions of metal coordination complexes are described. Depending on the salt, the base, final pH, and other ligands used, the metal coordination complex solutions exhibit different binding properties which can be tailored to the substrate and/or material being coated.

Solution 1

In this example, chromium perchlorate hexahydrate (45.9 g) was dissolved into 480 mL of purified water and mixed thoroughly until all solid dissolved. 8 mls of ethylene diamine solution was added to 490 mL of purified water. The solutions were combined and stirred overnight at room temperature, and then left to equilibrate to a pH of approximately 4.5.

Solution 2

In this example, chromium chloride hexahydrate (26.6 gm) was dissolved into 500 mL of purified water and mixed thoroughly until all solid dissolved. The pH was adjusted slowly to 4.5 with 1M NaOH or LiOH.

Solution 3

In this example, chromium chloride hexahydrate (45.9 g) was dissolved into 480 mL of purified water and mixed thoroughly until all solid dissolved. 8 mL of ethylene diamine solution was added to 490 mL of purified water. The solutions were combined and stirred overnight at room temperature, and then left to equilibrate to a pH of approximately 3.8.

In the above approaches, the ratios of the reagents could be adjusted to change the final pH of the solution and hence the characteristics of the metal-ligand coordination complex.

Example 2: Fluorescent 5-Carboxyfluorescein (First Agent) Binding to Metal Complex Activated Magnetic Particles A. Preparation of Metal Complex Activated Nanoparticles As an example, 250 nm magnetic nanoparticles purchased from Shanghai So-Fe Biomedicine Co., Cat No CSMN-250 were coated with metal complexes as described above (Example 1, Solution 1). The nanoparticles were allowed to reach room temperature and vortexed for 30 seconds. One millilitre of the stock particles were dispensed into a microtube. The tube was placed on a magnetic rack for 1 minute and the supernatant was carefully removed and discarded from the particle pellet. The particle pellet was resuspended with 100 μL of deionised water with 0.1% pluronic based surfactant. A further 900 μL of the metal complex solution was added giving a final concentration of 90 mM metal complex plus residual pluronic based surfactant. This was incubated overnight at 20-25° C. with rotation. Particles were pelleted on a magnet for 1 minute and the supernatant carefully removed. The particle pellet was then resuspended in 1000 μL of diluted (10 mM) metal complex solution. The pellet was resuspended by vortexing for 30 seconds and sonicating for 5 minutes on high. The metal complex activated particles were stored at 2-8° C.

B. Binding of 5-Carboxyfluorescein (First Agent) to Metal Complex-Activated Nanoparticles at Two Temperatures.

5-Carboxylflourescein purchased from Sigma (Product No. 86826-25MG-F), was reconstituted to 50 mg/mL in DMF. The 50 mg/mL stock solution of 5-Carboxyluorescein was diluted to 5 mg/mL in DMF and then to 2500 ug/mL in first agent solution (0.01% Pluronic based surfactant, 0.05% ProClin 300 in deionised water).

The metal complex activated particles were equilibrated to 20-25° C. and were vortexed for 10 seconds at high speed and sonicated for 5 minutes. A 250 μL aliquot of this stock metal complex activated particles (10 mg/mL) was dispensed into two micro-tube. The micro-tubes were placed on a magnetic rack for 1 minute and the supernatant removed. The particles tubes were then washed twice using 250 μL of first agent solution. Finally the particles were resuspended in 250 μL of first agent solution, vortexed for 10 seconds and pulse centrifuged to ensure the liquid was at bottom of tubes.

Aliquots of 250 μL of 2500 μg/mL 5-carboxylfluorescein were dispensed into two tubes. To these tubes, 250 μL of the metal complex activated particles was added into 5-carboxylfluorescein solution tubes (CF-25° C., CF-45° C.). The tubes were vortexed for 10 seconds and were placed on a rotatory mixer at 50 rpm for 60 minutes, one tube at 20-25° C. (R1-25° C.) and the other tube at 44.5° C. (R2-45° C.). Following this incubation, particles were vortexed for 10 seconds then separated from solution on a magnetic rack for 1 min, with the supernatant discarded. The particles were washed with 500 μL of first agent solution once. Finally particles were resuspended in 250 μL of first agent solution.

C. Competing 5-Carboxylfluorescein (First Agent) Using Various Concentrations of Mouse IgG as Competing Agent.

Mouse IgG (Lampire Biological Laboratories, Cat#7404304) standards were prepared in first agent solution (0.01% Pluronic based surfactant, 0.05% ProClin 300 in deionised water). The mouse IgG stock solution (10 mg/mL in PBS) was diluted to 1250 μg/mL (1:8), 250 μg/mL (1:5) and 50 μg/mL (1:5) in first agent solution. The negative control for competing agent having no mouse IgG were 10 mM PBS buffer diluted (1:8, 1:40, 1:200) in first agent solution.

A 25 μL aliquot of the metal complex activated particles (Positive control) was transferred into a tube labelled PC and 25 μL of the bare particles (Negative control) into a tube labelled NC. Both particles were washed twice with 25 μL of first agent solution. Finally particles were resuspended in 25 μL of first agent solution. To these tubes, 25 μL aliquots of each of the different concentrations of mouse IgG were dispensed into individually labelled (R1-25° C. or R2-45° C. with and without mouse IgG) microfuge tubes. See Table 1 for details of labelling. First agent solution (25 μL) was also dispensed into microfuge-tubes labelled (R1-CS, R2-CS). Similarly 10 mM PBS (1:8) in first agent solution was placed in tubes labelled (R1-PBS-1250, R2-PBS-1250), 10 mM PBS (1:40) in tubes labelled (R1-PBS-250, R2-PBS-250) and 10 mM PBS (1:200) in first agent solution in tubes labelled (R1-PBS-50, R2-PBS-50).

To tubes labelled (R1-Ab-1250, R1-Ab-250, R1-Ab-50, R1-CS, R1-PBS-1250, R1-PBS-250, R1-PBS-50) were added 25 μL of particles (R1-25° C.). To tubes labelled (R2-Ab-1250, R2-Ab-250, R2-Ab-50, R2-CS, R2-PBS-1250, R2-PBS-250, R2-PBS-50) were added 25 μL of the particles (R2-45° C.). As well, 25 μL of the particles (PC) were added into the tube (PC-Ab-250) and 25 μL of the particles (NC) were added into the tube (NC-Ab-250). All particles tubes were incubated with rotation at 50 rpm for 30 minutes at 20-25° C. The microfuge tubes containing the particle in various treatments were place on a magnetic rack for 1 minute and the supernatant transferred to new labelled microfuge tubes. (RSN1-Ab-1250 . . . RSN2-PBS-50). The particles were washed with 25 μL of first agent solution and then resuspended 25 μL of first agent solution.

TABLE 1

Experimental layout of Example 2 Study

| Sample ID | Particle | 5-Carboxyfluorescein concentration μg/mL | mouse IgG concentration μg/mL | PBS in conjugation solution mM | Reaction temperature during coated 5-Carboxyfluorescein to the particles |
|---|---|---|---|---|---|
| R1-Ab-1250 | metal complex | 2500 | 1250 | 1.25 | 20-25° C. |
| R1-Ab-250 | 250 nm magnetic particles | | 250 | 0.25 | |
| R1-Ab-50 | | | 50 | 0.05 | |
| R1-ddH2O | | | 0 | 0 | |
| R2-Ab-1250 | | | 1250 | 1.25 | 44.5° C. |
| R2-Ab-250 | | | 250 | 0.25 | |
| R2-Ab-50 | | | 50 | 0.05 | |
| R2-ddH2O | | | 0 | 0 | |
| R1-PBS-1250 | | | 0 | 1.25 | 20-25° C. |
| R1-PBS-250 | | | 0 | 0.25 | |
| R1-PBS-50 | | | 0 | 0.05 | |
| R2-PBS-1250 | | | 0 | 1.25 | 44.5° C. |
| R2-PBS-250 | | | 0 | 0.25 | |
| R2-PBS-50 | | | 0 | 0.05 | |
| PC-Ab-250 | | 0 | 250 | 0 | — |
| NC-Ab-250 | 250 nm PAA magnetic particles | | 250 | 0 | — |

D. Loading Assay of Competing Agent Using Goat Anti Mouse IgG-RPE.

Goat anti Mouse IgG-RPE (Jackson Immunoresearch Cat#115-116-072) was reconstituted at 0.5 mg/mL in deionised water. The particles (10 mg/mL) were diluted to 0.2 mg/mL in 1% BSA, 50 mM TBS, 0.05% Tween 20, pH8 (Assay buffer). The stock Goat anti Mouse IgG-RPE (0.5 mg/mL) was diluted to 2.5 μg/mL with assay buffer and 50 μL of the diluted particles were dispensed into a 96 well white U bottom plate (Greiner bio-one, Lot#13221155). To each well in rows A to D, was dispensed 50 μL of 2.5 μg/mL Goat anti Mouse IgG-RPE. Similarly 50 μL of assay buffer was dispensed into each well in rows E to H. The plate was incubated on a plate shaker for 30 minutes at 25° C. The plate was placed on a plate magnet for 5 minutes and the supernatant removed. The particles were then washed three times by the same process with 100 μL of washing buffer (50 mM TBS, 0.05% Tween 20, pH8) for each wash cycle. Finally 100 μL of washing buffer was added into all wells. The plate was shaken with the plate shaker for 1 minute. Absorbance values were read on TECAN (Infinite 200PRO)

with the settings of excitation wavelength at 546 nm and emission wavelength at 575 nm.

E. Results.

The standards for 5-Carboxyfluorescein were from series dilution starting from 2500 µg/mL of 5-Carboxyflourscein solution (see FIG. 1). The RSN1-Ab-1250 and RSN2-Ab-1250 were diluted (1:400) in first agent solution and other supernatants were diluted (1:100) in first agent solution.

Using a 96 well white U bottom plate (Greiner bio-one, Lot#13221155), the samples (100 µL per well) were read on TECAN (Infinite 200PRO) with excitation wavelength set at 492 nm and emission wavelength set at 517 nm.

Figure 2:
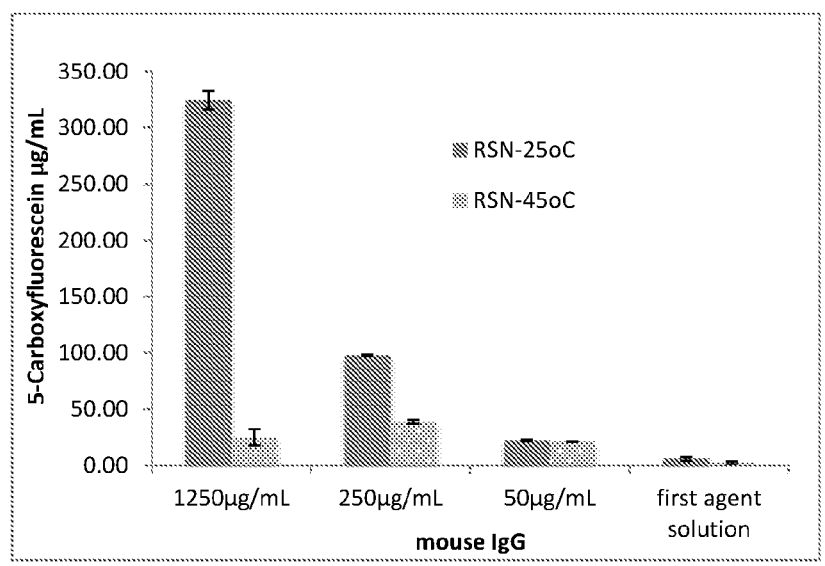
FIG. 2 is a graphical representation of 5-carboxyfluorescein release with various concentrations of mouse IgG in 10 mM PBS. 5-carboxyfluorescein binding was performed at two temperatures, 25° and 45° C. The data is corrected by subtracting the absorbance values due to PBS present in the mouse IgG buffer.
Figure 3:
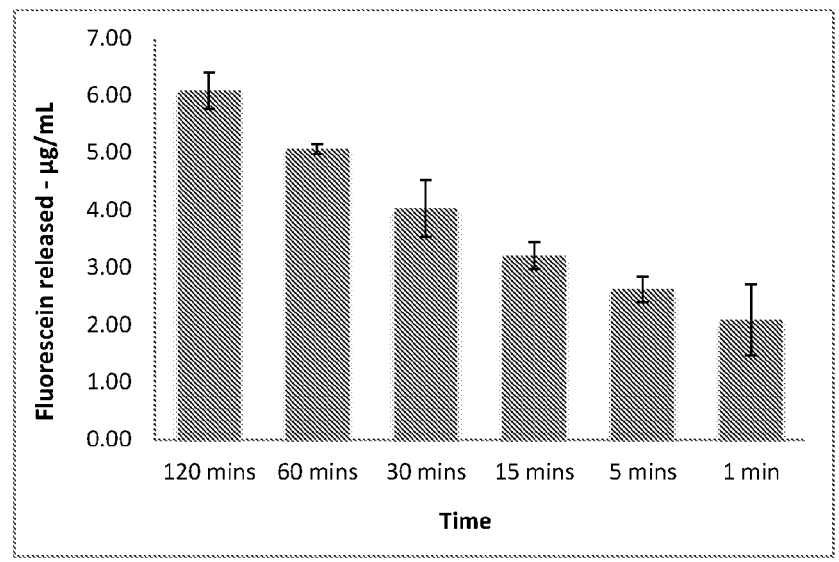
FIG. 3 is a graphical representation of 5-carboxyfluorescein release with time using 250 µg/ml concentration of mouse IgG in 10 mM PBS. The data is corrected by subtracting the absorbance values due to PBS present in the mouse IgG buffer.

The competitive release assay data is summarised for 5-carboxyfluorescein coated metal complex magnetic particles in FIGS. 2 and 3. As shown in FIG. 2, the assay of supernatants shows increasing mouse IgG concentration correlated with a greater release of 5-carboxyfluorescein from the particles into the supernatant. Release of 5-Carboxyfluorescein from the particles was significantly less when First Agent was bound at 45° C. compare to 25° C. demonstrating the use of temperature to control exchange reactions. FIG. 3 shows a time course of competitive exchange using mouse IgG at 250 µg/mL concentration showing competition of 5-carboxyfluorescein release was time dependent. These examples demonstrate the potential to control rate of release by controlling the conditions under which the first agent is bound to the metal coordination complexes and by the use of different concentrations of competing agents.

Figure 4:
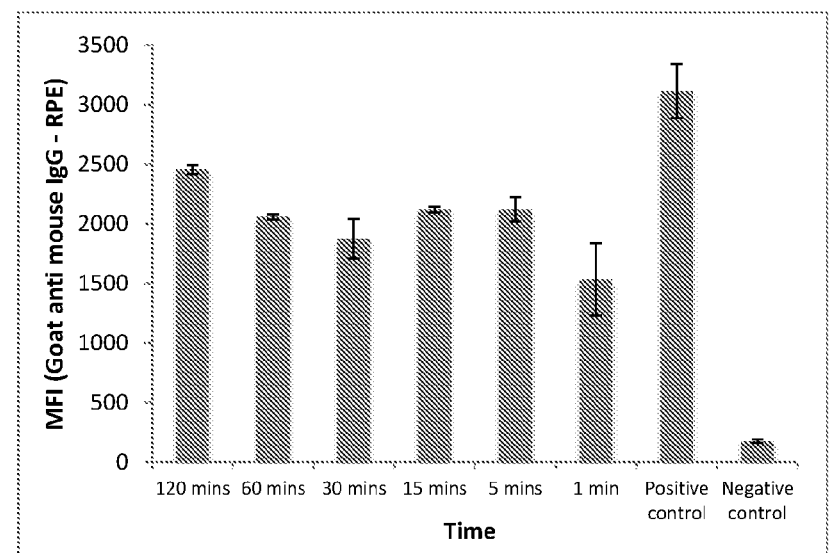
FIG. 4 is a graphical representation of the loading of mouse IgG resulting from the competitive release of 5-carboxyfluorescein using 250 µg/ml mouse IgG at various incubation times. The positive and negative controls are mouse IgG loading on non-5-carboxyfluorescein capped metal complex particles and non-mouse IgG bound particles, respectively.
Figure 5:
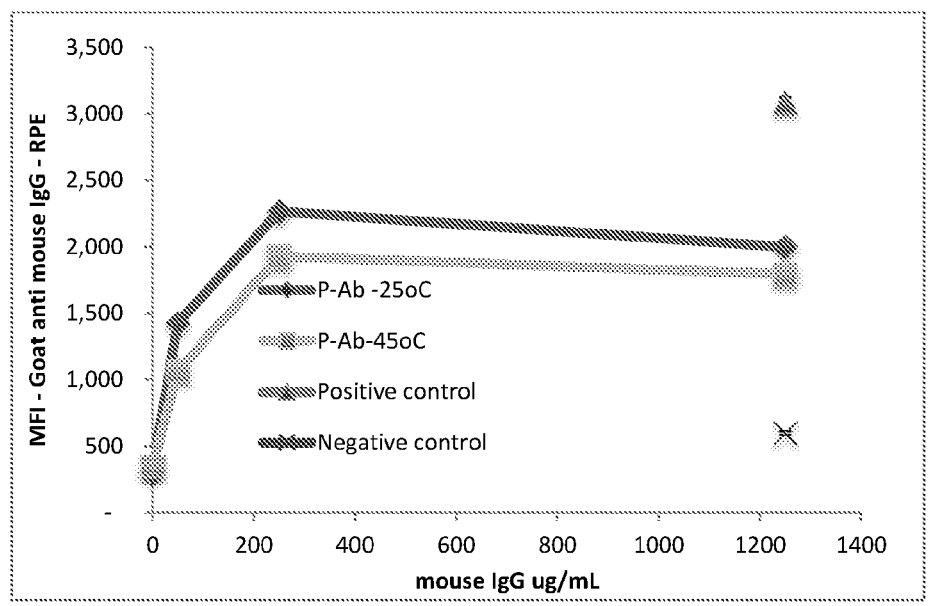
FIG. 5 is a graphical representation of the loading of mouse IgG resulting from different 5-carboxyfluorescein binding conditions (25° vs 45° C.) using various mouse IgG concentrations. The positive and negative controls are mouse IgG loading on non-5-carboxyfluorescein capped metal complex particles and non-mouse IgG bound particles, respectively.

As well as 5-carboxyfluorescein release, measurement of mouse IgG (competing agent) binding onto the metal complex particles was also assessed as described in Section D. Release of fluorescein from particles due to PBS was corrected for by subtracting the absorbance values for PBS only supernatants from the equivalent dilutions containing mouse IgG. FIG. 4 shows mouse IgG loading for the same time course shown in FIG. 3. The mouse IgG loading on metal complex particles (positive control) had significantly higher antibody loading signal than the fluorescein bound particles in this time course study implying there was still 5-carboxyfluorescein bound on metal complex particles after 120 minutes. The non-mouse IgG bound particles (negative control) gave very low antibody loading signal. FIG. 5 shows that particles coated with 5-carboxyfluorescein at 45° C. were more stable to competition compared with those coated at 25° C. Higher temperatures will further increase stability of binding of first agent. These examples demonstrate that competing agents are binding to the metal complex as the first agents are being released i.e. an exchange reaction is occurring.

Example 3: Binding Streptavidin on Acetate (First Agent) Capped Metal Complex-Activated Nitrocellulose Membranes A. Preparation of Acetate (First Agent) Capped Metal Coordination Complexes.

To metal complexes as described in Example 1 (Solution 1), sodium acetate was added in 2× fold molar excess with respect to molar concentration of chromium. For example, to 100 mls of metal complex solution from Solution 1 was mixed with sodium acetate (1.64 g, 20 mmoles) at RT. Sodium acetate was added gradually to a mixing solution and mixing continued for an hour.

B. Binding First Agent Capped Metal Complexes on Surfaces.

As an example, nitrocellulose membranes (Millipore Cat#HF090MC100) were fully wetted with acetate-capped and uncapped metal complex formulations as 10 mM solutions diluted in water. Untreated membrane controls were subjected to the same conditions as metal complex activated membranes. Both acetate and non-acetate capped membranes were allowed to partially dry for 1 hr at 23° C. at relative humidity of 23%.

C. Binding Streptavidin (Competing Agent) to Metal Complex Activated Nitrocellulose Membranes.

Capture ligand streptavidin at 0.1 mg/ml (Mybiosource Cat#142839) was applied using a CAMAG Linomat V at a rate of 1 uL/cm to all membranes. In this study, streptavidin was diluted in different striping buffers (carbonate, phosphate, MES or acetate, all at 10 mM) containing 1% sucrose. Streptavidin was fixed to membranes with heating @ 37° C. for one hour, followed by overnight drying at 23° C. with relative humidity of 23%. Membranes were then assembled with absorbent pads (Whatman Cat#8117-2550) and cut to 4 mm width with Biodot cutter CM3100. Membranes were blocked with 10% BSA (Ausgenex Cat# PBSA) in PBS buffer containing 0.1% Tween20.

Prior to study, Sp-biotin-mouse IgG (Jackson Immunoresearch Cat#015-060-003) was coated onto metal complex activated gold colloids (BBI solutions Cat#HDGC40) at a concentration of 3.2 ug/OD of gold. Conjugated gold was diluted to OD 0.25 in Tris-buffered saline, 1% Tween20 at pH 7.4. These gold colloids wicked up the strips in dipstick format and capture of Sp-biotin-mouse IgG gold to streptavidin was assessed using a densito-metric reader (Hamamatsu immunochromato-reader model: ICA1000).

D. Results

Figure 6:
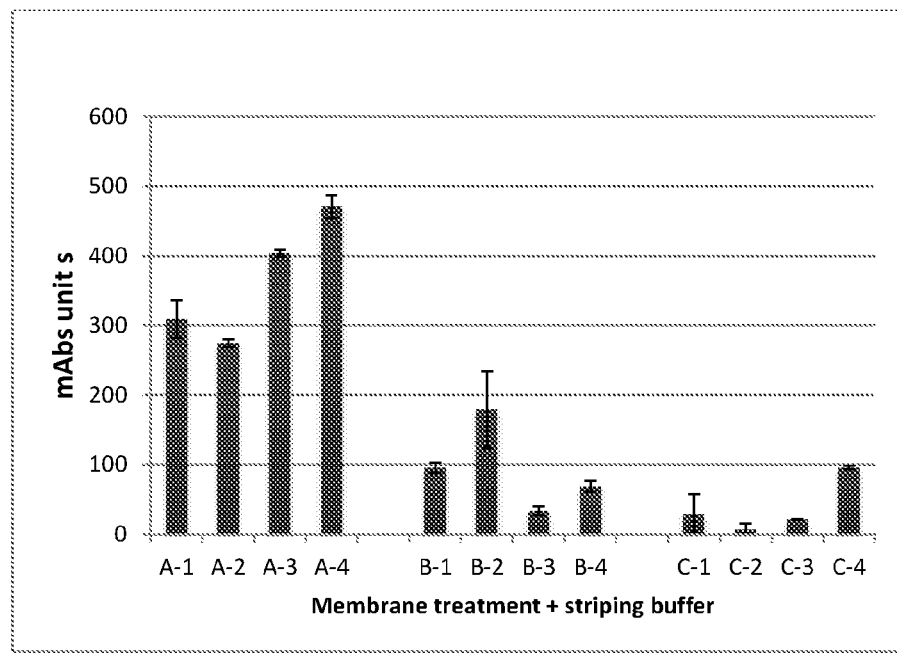
FIG. 6 is a graphical representation of the results of biotinylated mouse IgG on gold colloids being bound to streptavidin coated to A: acetate capped metal complex activated membranes, B: non-acetate capped, and C: untreated membranes. Striping buffers used were 1: 10 mM carbonate pH 9.2; 2: 10 mM phosphate buffer pH7.0; 3: 10 mM MES buffer pH 6.0; 4. 10 mM acetate buffer pH 4.5.

The results obtained in the above study are shown in FIG. 6. In the figure are shown, A: acetate capped metal complex activated membranes, B: non-acetate capped metal complex activated membranes, and C: untreated membranes. Striping buffers used were 1: 10 mM carbonate pH 9.2; 2: 10 mM phosphate buffer pH7.0; 3: 10 mM MES buffer pH 6.0; 4. 10 mM acetate buffer pH 4.5. As shown, the acetate capped metal complex activated membranes (A) captured far more conjugated gold colloids than the non-acetate capped metal complex activated membranes (B) or the passively coated membranes (C). This example clearly shows that there is greater availability of coordination sites to bind capture/target molecules when capped metal complexes are used in porous membranes.

Example 4: Binding Antibodies (TnI) on Acetate (First Agent) Capped Metal Complex-Activated Nitrocellulose Membranes A. First Agent Capped Metal Complex-Activated Membranes.

The first agent capped metal complex-activated nitrocellulose membranes used in this example were produced as described above.

B. Binding Antibodies to Metal Complex Activated Nitrocellulose Membranes.

To determine if treatment of nitrocellulose membranes with acetate capped metal complexes can improve performance of troponin lateral flow assay compared to untreated membranes, capture antibody for Control (goat anti-mouse IgG (Lampire Cat#7455527)) and anti-Troponin I (cTnI) monoclonal Ab 560 (Hytest Cat#4T21MAb560) were striped over the various activated membranes at 1 uL/cm.

The striping buffer for both antibodies were diluted to 1 mg/mL in 10 mM carbonate buffer pH 9.2 containing 1% sucrose. All reagents were applied to membranes using CAMAG Linomat V. Capture antibodies striped onto the membranes were fixed by heating @ 37° C. for one hour followed by drying overnight at 23° C. at relative humidity of 23%. Untreated membranes striped with the same preparations of capture ligands were exposed to the same conditions as metal complex activated membranes. Membranes were assembled with absorbent pad (Whatman cat#8117-2250) and cut to 4 mm strips with Biodot cutter (Model CM3100). The strips were stored in foil packs with desiccant until use.

The strips were evaluated using native cTnI (Hytest Cat#8T53) as the analyte and anti-cTnI MAb 19C7 (Hytest Cat#4T21MAb19C7) co-conjugated to colloidal gold with biotinylated bovine serum albumin (BSA), for detection. The strips were assayed in dipstick format with the strips being blocked before use with 50 uL of 10% BSA in PBS 0.1% Tween20. Dilutions of analyte (cTnI) from 0.05 ng/ml to 20 ng/mL as well as no antigen (negative) controls were mixed 1:1 with 19C7-biotin BSA gold OD1 in Tris-buffered saline with 1% Tween20. A total of 50 uL was allowed to wick up strip. Test signal was evaluated using a Hamamatsu Immunochromato-reader (model ICA-1000).

C. Results

Figure 7:
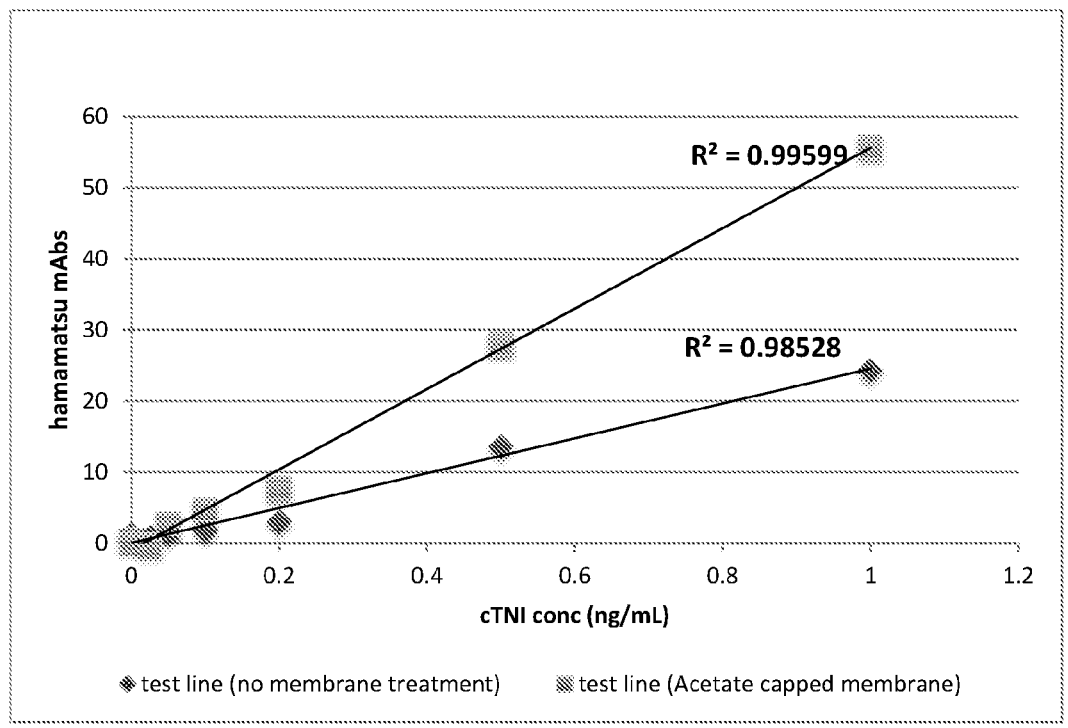
FIG. 7 is a graphical representation of the results of a troponin lateral flow assay on acetate capped metal complex activated membranes compared to untreated membranes. Membranes activated with uncapped metal complexes did not allow wicking up the membrane likely due to uncontrolled cross-linking and no signal was seen at the capture line.

The results obtained in the above study are shown in FIG. 7. Acetate capped metal complex activated membranes gave a two-fold increase in the signal to noise for detection of cTnI antigen compared to untreated membranes. Limit of detection of untreated membranes was 0.19 ng/mL compared to 0.08 ng/mL for the acetate capped metal complex activated membranes. Membranes activated with uncapped metal complexes did not allow wicking up the membrane likely due to uncontrolled cross-linking so they were not used for this LoD study as no signal was seen at the capture line. This example also shows that there is greater availability of coordination sites to bind capture/target molecules when capped metal complexes are used in porous membranes and shows the advantages over the typical passive binding approach of the prior art.

Example 5: Preparation of First Agent Capped Metal Complex-Activated Surfaces

A. Preparation of Phenylalanine (Phe) Capped Metal Coordination Complexes.

To metal complexes as described in Example 1 (Solution 1), phenylalanine was added in 5× fold molar excess with respect to molar concentration of chromium. For example, to 50 mls of metal complex solution from Solution 1 was mixed with 50 mls of a phenylalanine (4.13 g, 25 mmoles) solution at RT.

B. Binding First Agent Capped Metal Complexes on Surfaces.

As an example substrate, a hydrophobic plastic, COC, was incubated with capped metal complex solutions. The above solutions were diluted in water to give 1 and 5 mM capped metal complex solutions. The COC surface was submerged in diluted metal coordination complex for sixty minutes and washed in deionised water by dip immersion five times. The surface was then dried for sixty minutes in a low humidity chamber (RH<10%) and was then ready to use.

Contact angles were measured utilising a Dataphysics system after addition of 1 μL of deionised water to the COC surface. Contact angle measurements of First Agent capped metal complexes are presented in Table 2.

TABLE 2

Contact angles obtained on COC surfaces with and without Phe (first agent) capped metal complexes.

| Reagent | Contact Angle (°) |
|---|---|
| Bare COC surface | 98 |
| Uncapped 10 mM Metal Complex | 90 |
| Uncapped 1 mM Metal Complex | 96 |
| Phe capped 5 mM Metal Complex | 68 |
| Phe capped 1 mM Metal Complex | 84 |

C. Competing First Agent Capped Metal Complexes on Surfaces.

An antibody solution prepared at 120 μg/ml was spotted (2 nL) using a Scienion sciFLEXARRAYER S5 onto the capped and uncapped metal complex treated COC surface, onto the bare COC surface (negative control), and the antibody spot diameter was measured. The spot diameter for the capped metal complex treated COC surface was on average 220 μm and the uncapped metal complex treated COC surface was on average 190 μm. The spot diameter for the untreated COC surface was less than 190 μm.

These examples show that capping group can change the binding of metal complexes to COC and change the surface properties for binding proteins such as an antibody.

Example 6: Binding Proteins on First Agent Capped Metal Complex-Activated Microtitre Plates A. Preparation of First Agent Capped Metal Complexes on Microtitre Plates.

Polystyrene 96 well flat bottom plates (Corning costar Cat#2592) were activated by first coating metal coordination complexes, then polyacrylic acid and then more metal coordination complexes on the surface of the plate. Metal coordination complexes (Example 1, Solution 3) were diluted to a 10 mM solution, and 100 μL applied to each well. The coated plates were incubated at 20-25° C. for one hour. This solution was then aspirated and replaced with a 100 μL/well of 1 mg/mL solution of polyacrylic acid, MWt 450,000 (Sigma Cat#181285) in 10 mM MES buffer pH6.0. The polyacrylic acid coated plates were incubated for 1 hour at 20-25° C., and then aspirated and replaced with 100 μL/well of more 10 mM metal complex solution. This was again incubated for 1 hour at 20-25° C., then aspirated and the plate rinsed once with 200 μL/well of distilled water. Residual fluid was removed by tapping the inverted plate on paper toweling. The activated plate was dried overnight at 20-25° C., relative humidity 23%, then stored in desiccant until used. Untreated plates from the same batch used for the above metal coordination complex activation were also retained as experimental controls, to be used for passive coating of primary reagent.

B. Coating Metal Complex Coated Plates with First Agent.

Four different potential first agents were coated onto the metal complex activated plates to demonstrate the varying affinity of binding of first agents to the metal complex activated surface. First agents included 10 mM MES buffer pH6, 100 mM phosphate buffer pH6, 2 mg/mL Dalteparin (Sigma Cat# D00700000) in 10 mM MES buffer and 2 mg/mL Bovine Serum Albumin (BSA) (Sigma Cat# A7030). 100 μL/well of each first agent was added to selected wells on both metal complex activated plates and untreated plates.

These plates were then sealed with a plate sealer and incubated at either 20-25° C. or 47° C. for 1 hour. The first agent solutions were then aspirated and the plates rinsed once with 200 μL distilled water.

C. Competitive Release of First Agent by Competing Agent.

Competition was evaluated using bovine serum albumin, BSA (Sigma Cat#A7030) and goat anti-mouse horse radish peroxidase, GAM-HRP (Jackson Immunoresearch Cat#115035003). GAM-HRP was used at a weight to weight ratio of 1:1000 with BSA. A matrix of conditions for competition was evaluated. Three concentrations of competing agent were used. One was BSA at 1 mg/mL and GAM-HRP at 1 ug/mL diluted in 10 mM MES buffer pH6, another was 100 ug/mL BSA with 0.1 ug/mL GAM-HRP in 10 mM MES buffer pH6 and the third was 10 mM MES buffer alone. Different periods for release were also examined including 10 minutes, 30 minutes and 60 minutes for all the above concentrations. All competition was performed at 25° C. with 100 uL of the competing agent added per well. The competition conditions were replicated on both metal complex activated plates and untreated plates coated with first agents. All plates were washed 4 times with phosphate buffered saline tween 20 (0.05%) (PBST). Binding of BSA-GAM-HRP to the plates was detected by the addition of TMB substrate (Surmodics Cat#TMBW-1000-01) 100 uL/well, incubated at 20-25° C. for 3 minutes. Colour development was stopped with the addition of 100 uL of 1M phosphoric acid. Absorbance was read at 450 nm on a Tecan infinite 200 pro plate reader.

Statistical analysis was performed using a Student's t-Test in Excel. The test parameters were using a 2-tailed distribution, with a two-sample unequal variance (heteroscedastic) test, comparing the release measurements of the primary agents with the MES only control samples.

Results

Figure 8A:
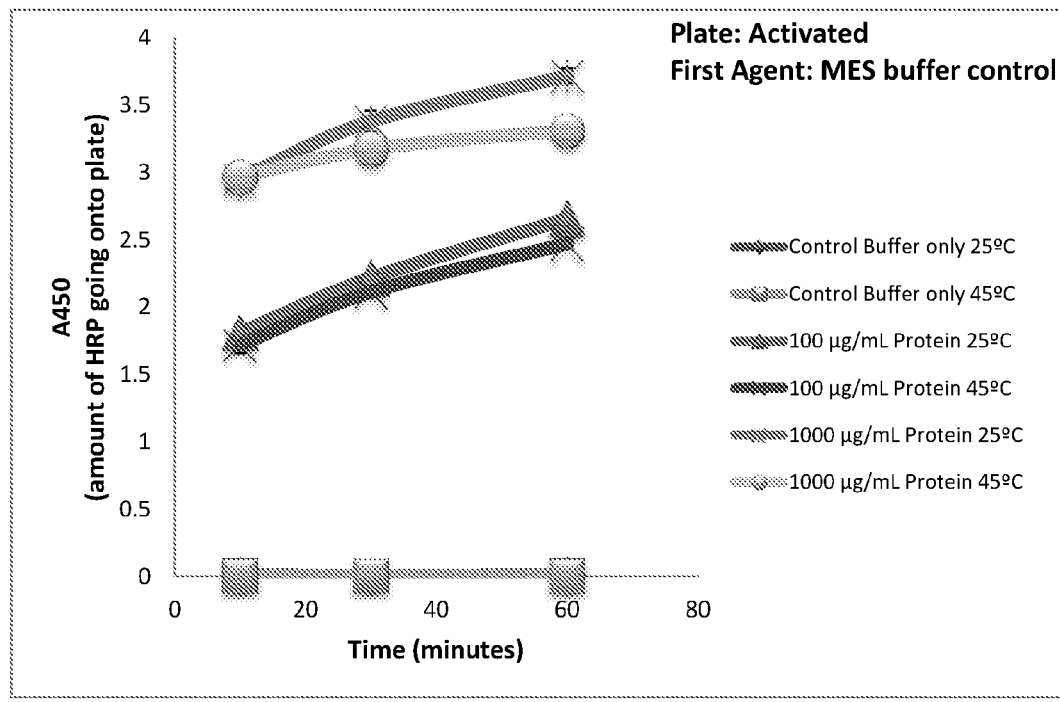
FIGS. 8 A & B are a graphical representation of the results of bound GAM-HRP per well after "competition" with MES "capped" metal complex plates (A) vs passive coated plates (B) at different time points. Two MES binding conditions were used (25° vs 45° C.). These are controls for stronger First Agents.
Figure 8B:
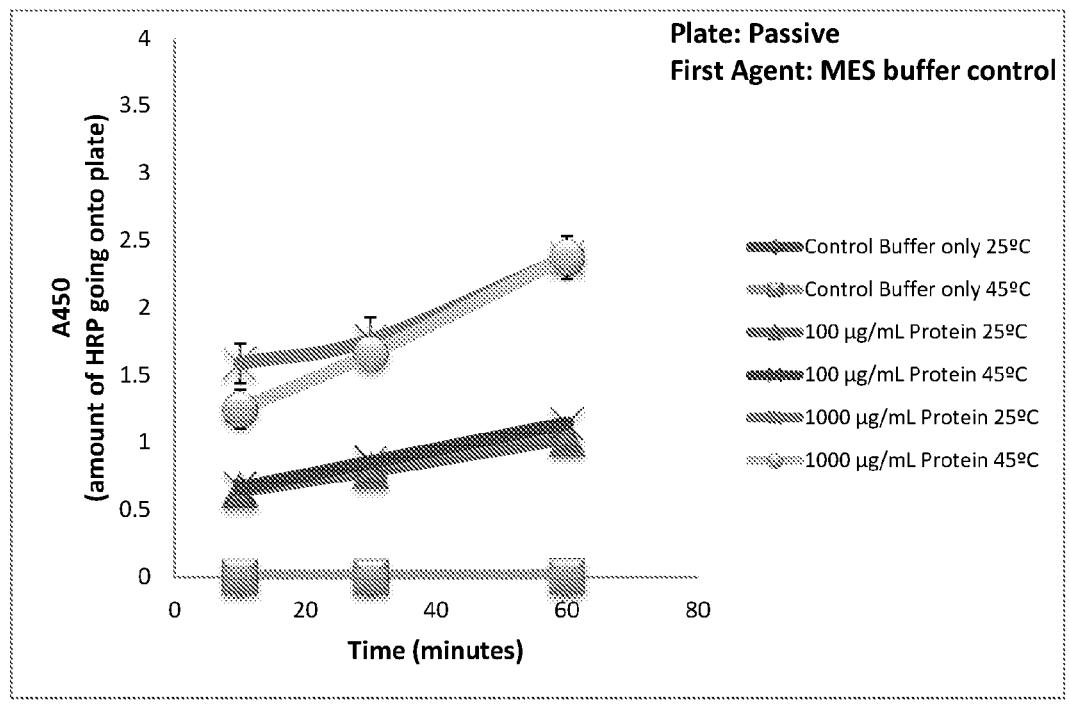
Figure 9A:
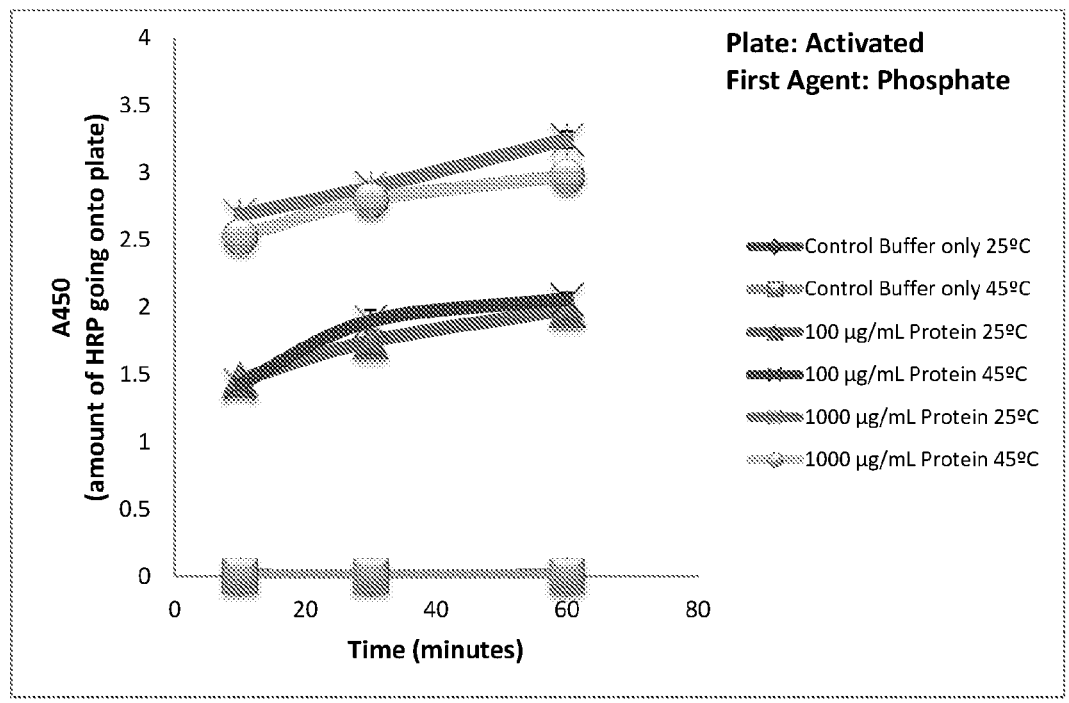
FIGS. 9 A & B are a graphical representation of the results of bound GAM-HRP per well after competition with PBS capped metal complex plates (A) vs passive coated plates (B) at different time points. Two PBS binding conditions were used (25° vs 45° C.)
Figure 9B:
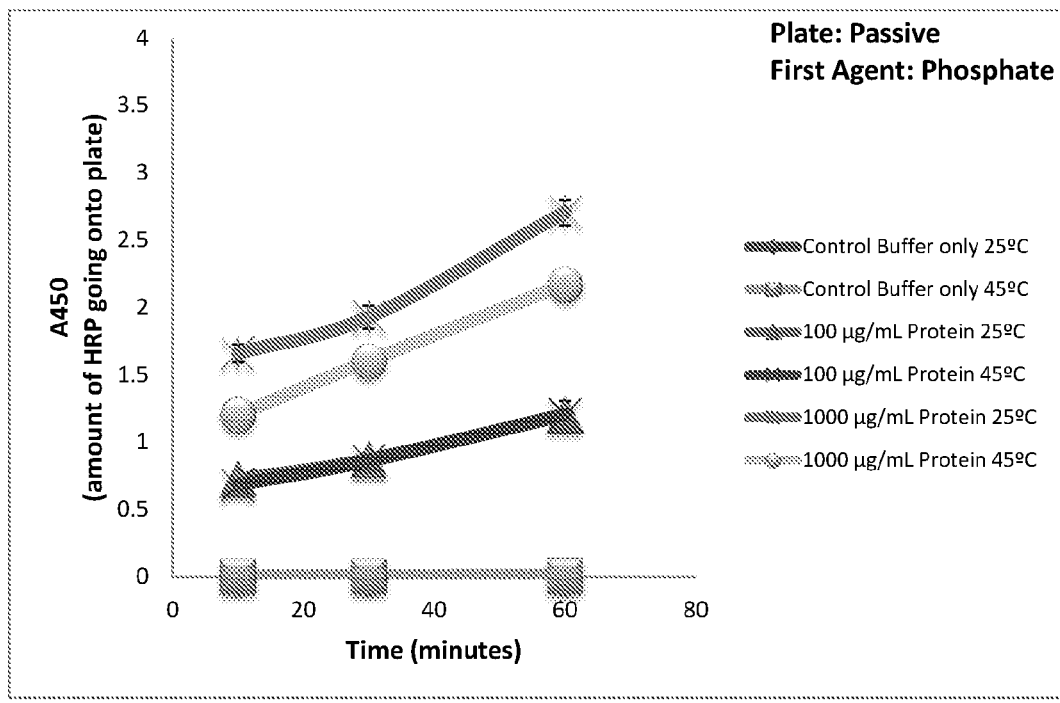
Figure 10A:
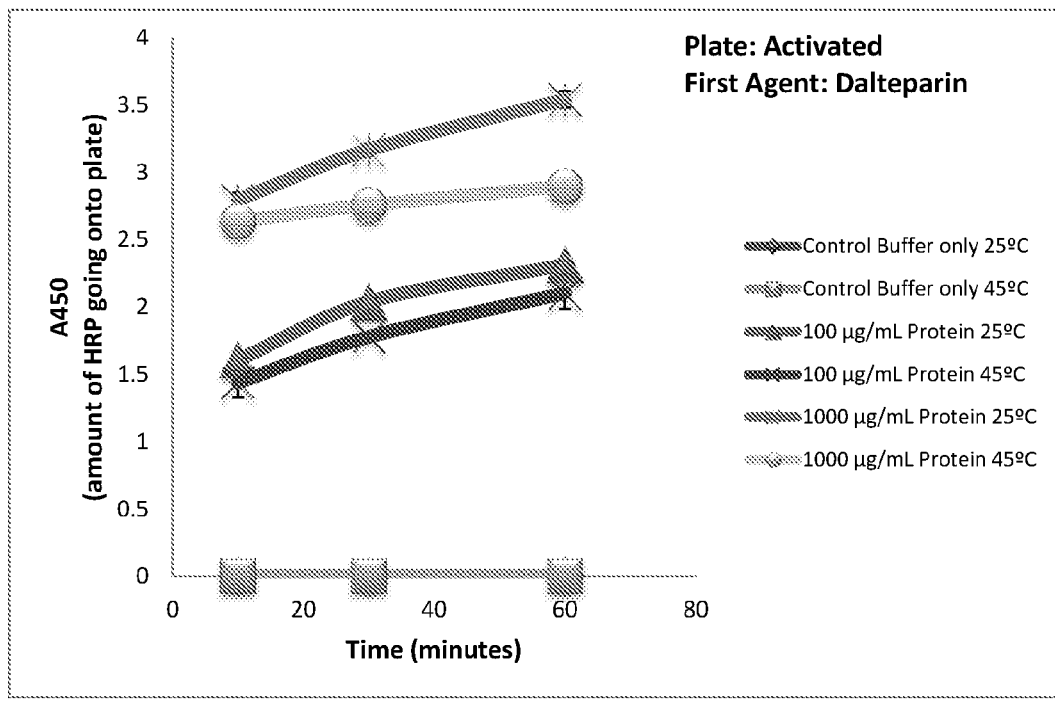
FIGS. 10 A & B are a graphical representation of the results of bound GAM-HRP per well after competition with Delteparin capped metal complex plates (A) vs passive coated plates (B) at different time points. Two Delteparin binding conditions were used (25° vs 45° C.)
Figure 10B:
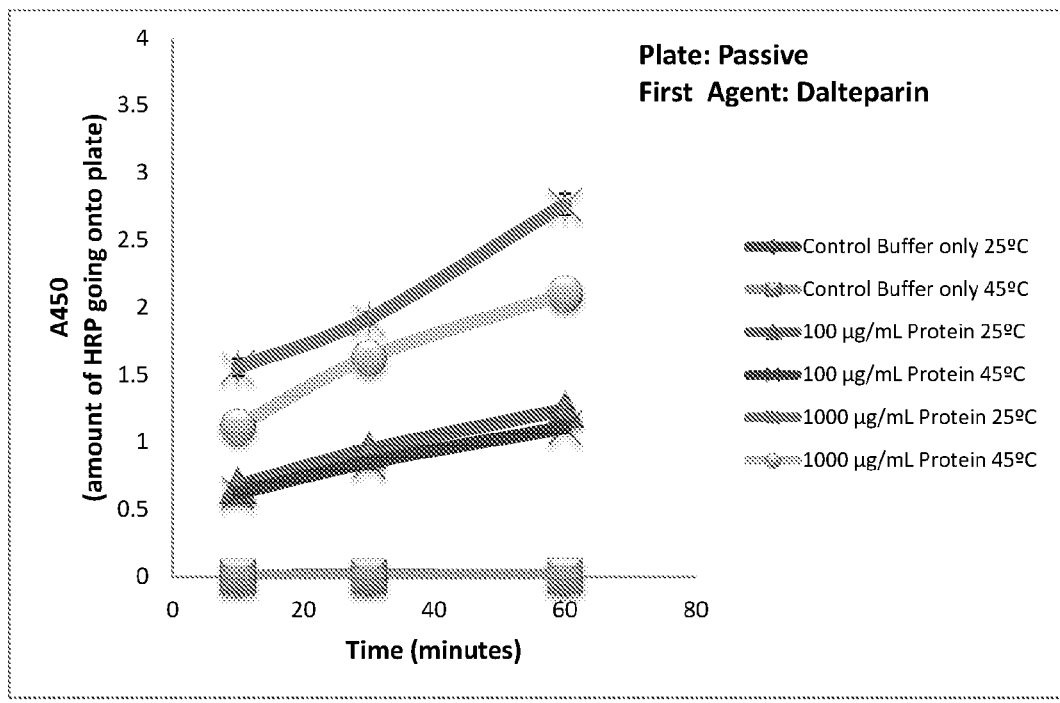
Figure 11A:
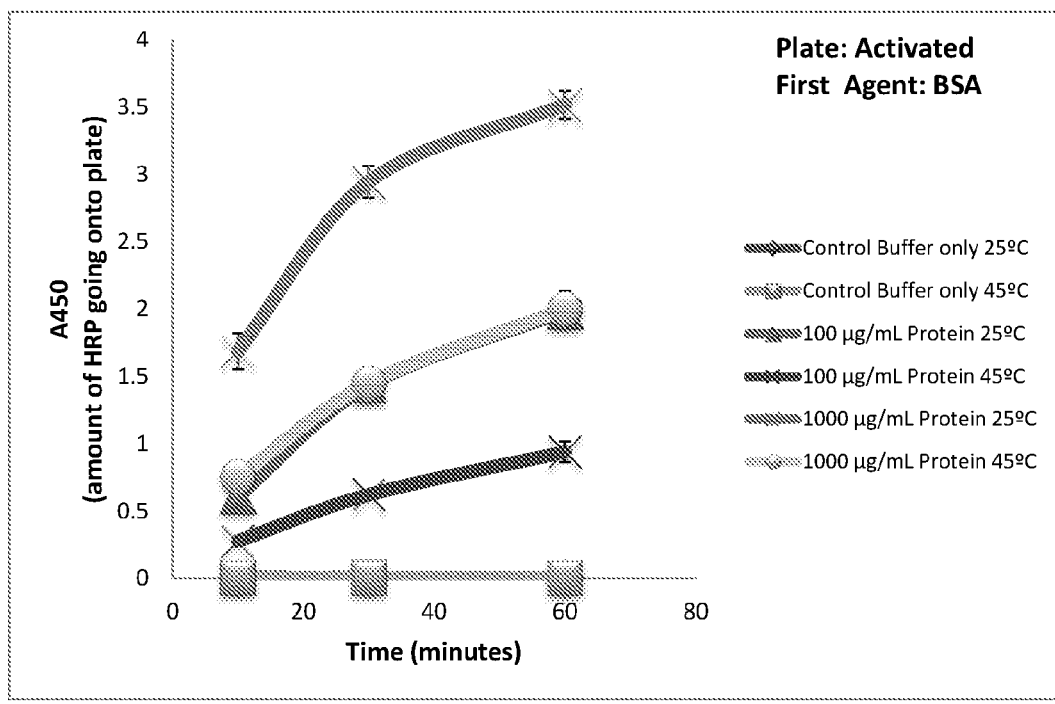
FIGS. 11 A & B are a graphical representation of the results of bound GAM-HRP per well after competition with BSA capped metal complex plates (A) vs passive coated plates (B) at different time points. Two BSA binding conditions were used (25° vs 45° C.)
Figure 11B:
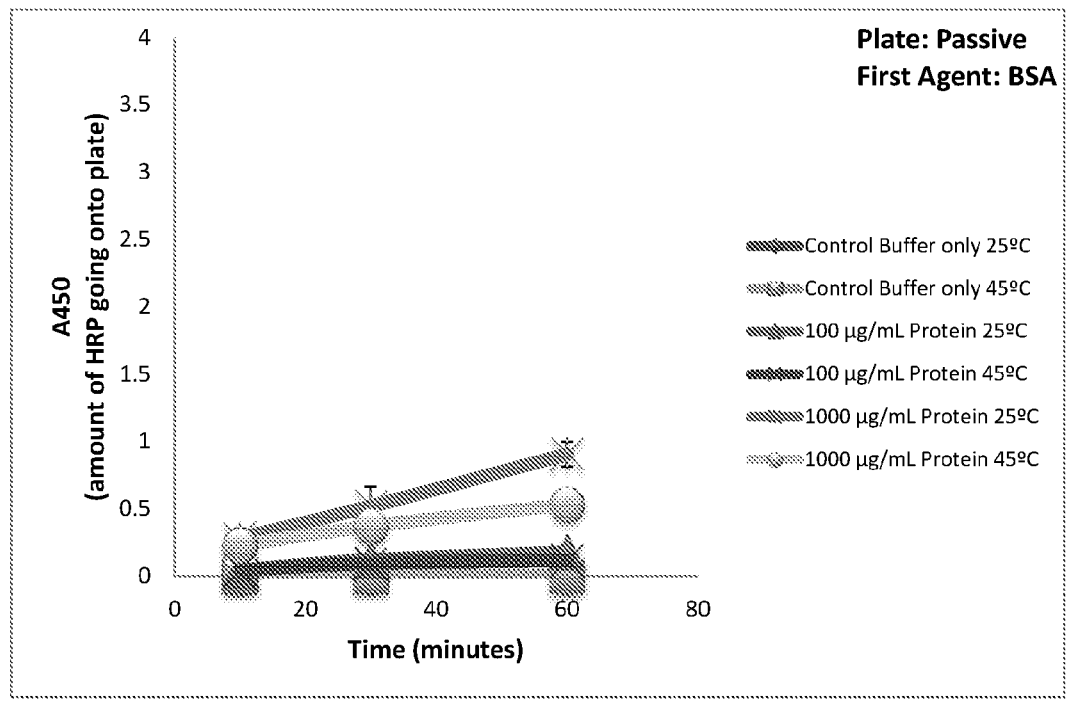

FIGS. 8 A & B, 9 A & B, 10 A & B and 11 A & B show the differences obtained with different first agents, MES (Control), PBS, Dalteparin and BSA bound at two temperatures on metal complex activated plates vs passive plates, respectively. Release profiles graph out HRP signal (y axis) which is a direct readout of the amount of bound GAM-HRP to the well, at different time points of incubated competing agent (x axis). y axis standard deviation error bars are included.

Using a probability cut off of 0.05, first agent and conditions of first agent binding give significantly different outcomes compared to controls utilising passive binding on microtitre plates.

Example 7: Binding Antibiotic Rifampicin (First Agent) to Metal Complex-Activated Polyurethane A. Activation of Polyurethane Tubing with Metal Coordination Complexes.

Polyurethane tubing (ARK-plas product inc Cat#TAX36-ANL) was cut into 1 cm lengths with replicates of three in each treatment group. One of these treatment groups underwent no activation treatment for the tubing and served as a negative control for metal complex activation. The other two treatment groups were first immersed in a 5 mM solution of metal coordination complex (Example 1, Solution 1) for 1 hour at 20-25° C. Treated tubing was removed from the hydrophilic metal complex and excess fluid removed. Substituted metal complexes as described in PCT publication WO 2015/192183 was diluted to 5 mM in a 1:1 mix of water and isopropanol. Treated tubing was then immersed this solution for 1 hour at 20-25° C. Tubing was removed from solution, blotted to remove residual solution and cured at 37° C. for 15 minutes and then dried overnight at 20-25° C. with desiccant.

B. Creation of Encapsulated Antibiotic-Metal Polymer-Polyacrylic Acid Complexes

Antibiotic rifampicin (Sigma Cat#R3501) was reconstituted to 100 mg/mL in DMSO (Sigma Cat#D8414). It was subsequently diluted in water to 2.5 mg/mL. Metal complex (Example 1, Solution 1) was diluted to 50 mM in water. The diluted rifampicin solution and diluted metal complex were mixed at a 1:1 ratio (vol:vol) on a rotary mixer at 20 rpm for 1 hr. This combined rifampicin, metal complex mix was then combined with polyacrylic acid 450 kilodalton (Sigma Cat#181285), diluted to 0.8 mg/mL in 25 mM MES pH5, at a 1:1 ratio (vol:vol). The final ratio of volumes of rifampicin: metal complex polymer:polyacrylic acid solution is 1:1:2. The metal complex, rifampicin, polyacrylic acid combination was mixed on a rotary mixer at 20-25° C. for 1 hour.

C. Coating of Metal Complex Activated Polyurethane Tubing with Either Antibiotic Alone or Encapsulated Antibiotic Complexes Three different methods were used for coating rifampicin onto the polyurethane tubing. Treatment A was used for the untreated polyurethane tubing. The tubing was immersed in a 0.625 mg/mL solution of rifampicin in water. The tubing and solution were heated to 60° C. in a bead bath with intermittent mixing for 1 hour. The rifampicin solution was discarded, excess fluid removed from tubing by blotting and tubing dried at 37° C. for 15 minutes followed by overnight drying in a desiccant cabinet at 20-25° C. Treatment B was applied to metal complex activated tubing under the same conditions as Treatment A. Treatment C was the immersion of metal complex activated tubing in the encapsulated rifampicin-metal polymer-polyacrylic acid complex solution, described above. The tubing was incubated at 60° C. in the rifampicin-metal polymer-polyacrylic acid solution for 1 hour with intermittent mixing. The tubing was then removed from the solution and excess solution removed by blotting. Tubing was then dried at 37° C. for 15 minutes followed by overnight drying at 20-25° C. in a desiccant cabinet. The difference between the three treatments is summarised in the able below.

D. Elution of Antibiotics from Polyurethane Tubing.

Treated tubing was first washed for 5 minutes in phosphate buffered saline (Sigma Cat#P3813) with 10 second vortex to remove unbound rifampicin (pre-wash). This was then followed by sequential washing in PBS. Triplicate tubing segments were each immersed in 1 mL of PBS and incubated overnight at 37° C. (24 hrs). The tubing segments were then removed and placed in fresh PBS for another overnight incubation at 37° C. (48 hrs with fresh PBS). The supernatants from these washing steps were stored at −80° C. until evaluated for rifampicin concentration.

E. Results.

Rifampicin shows absorbance peaks at 237, 255, 334, 475 nm. Minimal interference with metal complexes and polyacrylic acid was seen at 475 nm, so this wavelength was used to estimate quantities of rifampicin in the eluted solutions. A rifampicin standard curve was generated by diluting rifampicin of a known concentration in the same buffer used for elution of rifampicin from tubing. The concentration of rifampicin in the eluates from the tubing was then interpolated from the standard curve generated from dilutions of rifampicin standard using Graph pad prism version 6.

Figure 12:
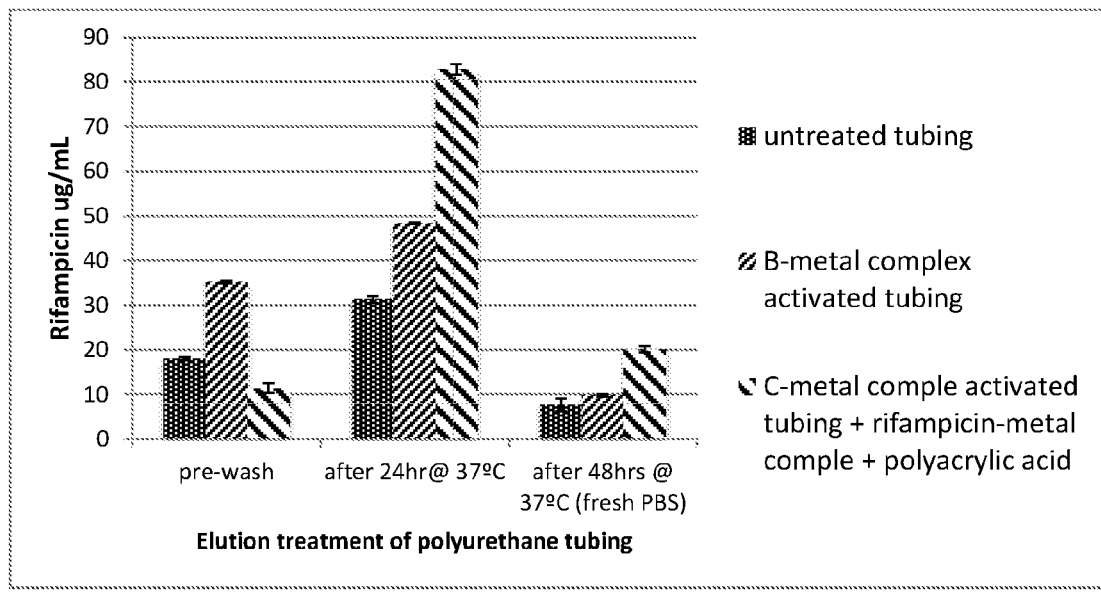
FIG. 12 is a graphical representation showing the release of rifampicin into PBS under various conditions. Treatment C retains significantly more rifampicin and is able to release more rifampicin when incubated at 37° C. for 24 hrs, and still has more rifampicin release when incubated at 37° C. with fresh PBS for a further 24 hrs.

As shown in FIG. 12, there is greatest loading of rifampicin for treatment group C (tubing activated with metal polymers, combined with rifampicin-metal-polymer-polyacrylic acid complexes), followed by treatment group B (metal-polymer activated tubing) with the least amount of rifampicin on group A (untreated tubing). Even with the greater loading of rifampicin on the treatment group C this group showed the lowest shedding of rifampicin in the pre-wash (student's t test: P<005). For both the first and second overnight incubation in PBS at 37° C. (24 hrs and 48 hrs with fresh PBS) treatment group C had the best capacity for release of rifampicin into the solution. It was statistically different to treatment group A and group B by student's t test for both the first and second incubation steps (P<0.05).

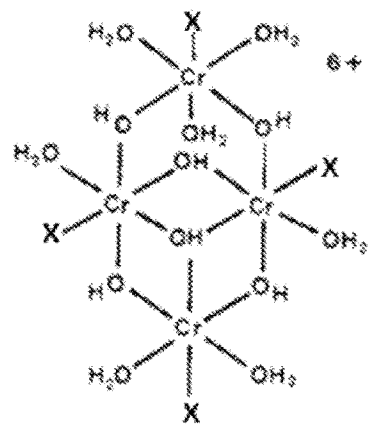

The invention claimed is:

1. A method of controlled competitive exchange of a bound first agent and a competing agent including the steps of:
   (a) providing an oligomeric metal coordination complex having one or more ligands bound to the metal of the oligomeric metal coordination complex;
   (b) exposing the oligomeric metal coordination complex with bound one or more ligands to the first agent to thereby have the first agent exchange with the one or more ligands; wherein the first agent is selected for its coordination strength to the oligomeric metal coordination complex and is coordinately bound thereto, and wherein the first agent is a therapeutic agent or a capping agent; wherein the capping agent is an agent comprising a dative bond forming group which is an oxygen containing group;
   wherein either the oligomeric metal coordination complex of (a) or the oligomeric metal coordination complex with bound first agent of (b) is coated onto a substrate, wherein the substrate is a metal, metal alloy, glass or polymer substrate, and wherein the oligomeric metal coordination complex is coordinately bound to a surface of the substrate; and
   (c) exposing the substrate-bound oligomeric metal coordination complex with bound first agent to the competing agent in solution, the competing agent having a greater coordination strength with the oligomeric metal coordination complex than the first agent,
   wherein the competing agent has a greater number of electron donating sites than the first agent to thereby allow the competing agent to become preferentially bound to the oligomeric metal coordination complex by exchanging with the first agent, and wherein the nature of the first agent and the competing agent are selected, with respect to one another, such that the exchanging occurs over a desired time period.

2. The method of claim 1 wherein the molecular mass ratio of the competing agent to the first agent is greater than about 10:1.

3. The method of claim 1 wherein the molar ratio of coordination ligands on the competing agent to those on the first agent is greater than about 10:1.

4. The method of claim 1 wherein the first agent is selected from the group consisting of a bidentate and tridentate agent.

5. The method of claim 1 wherein the competing agent is a large biomolecule or a fragment thereof.

6. The method of claim 5 wherein the competing agent has a molecular mass of greater than 20,000 Daltons.

7. The method of claim 1 wherein the first agent is modified with a tag to increase its molecular weight and/or electron-donating capacity.

8. The method of claim 1 wherein the first agent has a greater molecular mass and/or coordination strength for the oligomeric metal coordination complex and/or number of electron donating sites and/or electron density than the one or more ligands.

9. The method of claim 1 wherein the oligomeric metal coordination complex comprises a metal ion selected from the group consisting of chromium, ruthenium, iron, cobalt, aluminium, zirconium and rhodium.

10. The method of claim 1 wherein the competing agent is a capture molecule adapted to bind a target molecule from a biological sample.

11. The method of claim 3 wherein the molar ratio of coordination ligands on the competing agent to those on the first agent is greater than about 100:1.

12. The method of claim 1 wherein the selecting of the first agent for its coordination strength to the oligomeric metal coordination complex comprises a selection based on the number of electron donating sites the first agent presents.

13. The method of claim 1 wherein the substrate is a porous material.

14. The method of claim 13 wherein the porous material is a porous cellulose-based substrate.

15. The method of claim 1 further including the step of controlling the exchange of the first agent by the competing agent by one or more of: (i) selecting the temperature at which the competing agent is exposed to the oligomeric metal coordination complex with bound first agent; (ii) selecting the concentration of the competing agent to which the bound first agent is exposed; and (iii) selecting the time period for which the competing agent is exposed to the bound first agent.

16. The method of claim 1, wherein the oxygen containing group of the capping agent is selected from the group consisting of a sulphate, a phosphate, a carboxylate, a sulphonic acid and a phosphonic acid.

17. The method of claim 1, wherein the first agent is a capping agent selected from the group consisting of formate, acetate, propionate, oxalate, malonate, succinate, maleate, sulphate, phosphate and hydroxyacetate.

18. The method of claim 1, wherein the first agent is acetate.

19. The method of claim 1, wherein the one or more ligands comprise ethylenediamine.

20. The method of claim 1 wherein the oligomeric metal coordination complex comprises a chromium metal ion.

* * * * *

UNITED STATES PATENT AND TRADEMARK OFFICE
CERTIFICATE OF CORRECTION

PATENT NO. : 11,202,835 B2  
APPLICATION NO. : 15/777327  
DATED : December 21, 2021  
INVENTOR(S) : Huang et al.

Page 1 of 2

It is certified that error appears in the above-identified patent and that said Letters Patent is hereby corrected as shown below:

In the Specification

Column 22, Lines 32-42: Please delete chromium structure 6+ and replace with the following:

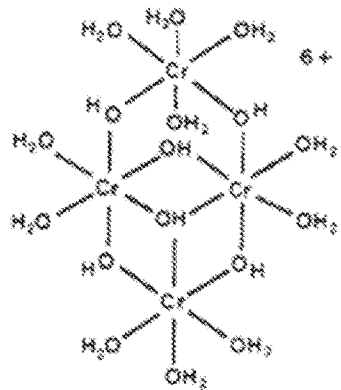

Column 23, Lines 1-12: Please delete chromium structure 6+ and replace with the following:

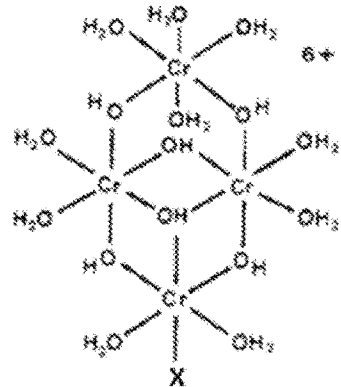

Signed and Sealed this  
Eighteenth Day of April, 2023

Katherine Kelly Vidal  
*Director of the United States Patent and Trademark Office*

CERTIFICATE OF CORRECTION (continued)

Column 23, Lines 33-42: Please delete chromium structure 6+ and replace with the following: